(12) United States Patent
McRuer et al.

(10) Patent No.: US 10,676,782 B2
(45) Date of Patent: *Jun. 9, 2020

(54) TRANSLOCATION CONTROL FOR SENSING BY A NANOPORE

(71) Applicant: Stratos Genomics, Inc., Seattle, WA (US)

(72) Inventors: Robert N. McRuer, Mercer Island, WA (US); Mark Stamatios Kokoris, Bothell, WA (US)

(73) Assignee: STRATOS GENOMICS, INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/569,472

(22) Filed: Sep. 12, 2019

(65) Prior Publication Data

US 2020/0002754 A1    Jan. 2, 2020

Related U.S. Application Data

(63) Continuation of application No. 15/311,149, filed as application No. PCT/US2015/030797 on May 14, 2015, now Pat. No. 10,457,979.

(Continued)

(51) Int. Cl.
 *C12Q 1/6825* (2018.01)
 *C12Q 1/6869* (2018.01)
 (Continued)

(52) U.S. Cl.
 CPC ......... *C12Q 1/6825* (2013.01); *C12Q 1/6869* (2013.01); *G01N 27/44704* (2013.01);
 (Continued)

(58) Field of Classification Search
 None
 See application file for complete search history.

(56) References Cited

U.S. PATENT DOCUMENTS 6,033,850 A    3/2000  Purvis
6,627,067 B1 *  9/2003  Branton ................ B24B 37/013
                                              204/403.06
(Continued)

FOREIGN PATENT DOCUMENTS

WO       01/42782 A1    6/2001
WO    2006/020775 A2    2/2006
(Continued)

OTHER PUBLICATIONS

An et al, Proc. Nat. Acad. Sci. USA, vol. 109, pp. 11504-11509, Jul. 17, 2012.*

(Continued)

*Primary Examiner* — Robert T. Crow
(74) *Attorney, Agent, or Firm* — Seed IP Law Group LLP

(57) ABSTRACT

Translocation control for sensing by a nanopore, as well as methods and products related to the same, are provided. Such methods optimize duplex stability to provide high fill rate (of the hybridization sites) but do not prevent rapid dissociation required for high read rates, as well as controlling the translocation of a target molecule for sensing by a nanopore by use of a selective pulsed voltage. Products related to the same include a reporter construct comprising two or more phosphoramidites.

21 Claims, 21 Drawing Sheets

Specification includes a Sequence Listing.

Related U.S. Application Data

(60) Provisional application No. 61/996,824, filed on May 14, 2014.

(51) Int. Cl.
  *G01N 27/447*  (2006.01)
  *G01N 33/487*  (2006.01)

(52) U.S. Cl.
  CPC . *G01N 27/44791* (2013.01); *G01N 33/48721* (2013.01); *C12Q 2565/631* (2013.01)

(56) References Cited

U.S. PATENT DOCUMENTS

| | | | |
|---|---|---|---|
| 7,939,259 | B2 | 5/2011 | Kokoris et al. |
| 10,457,979 | B2 * | 10/2019 | McRuer ........... G01N 27/44704 |
| 2009/0029477 | A1 | 1/2009 | Meller et al. |
| 2009/0104614 | A1 | 4/2009 | Tsourkas et al. |
| 2012/0214256 | A1 | 8/2012 | Merriman et al. |
| 2013/0092541 | A1 | 4/2013 | Drndic et al. |

FOREIGN PATENT DOCUMENTS

| | | |
|---|---|---|
| WO | 2006/028508 A2 | 3/2006 |
| WO | 2011/097028 A1 | 8/2011 |
| WO | 2012/003330 A2 | 1/2012 |
| WO | 2012/088339 A2 | 6/2012 |
| WO | 2013/162026 A1 | 10/2013 |
| WO | 2014/071250 A1 | 5/2014 |

OTHER PUBLICATIONS

Derrington et al., "Nanopore DNA sequencing with MspA," *PNAS*, 107(37): 16060-16065 (Sep. 14, 2010).

Ma et al., "Biological Nanopores for Single-Molecule Biophysics," *ChemBioChem*, 11(1): 25-34 (Jan. 4, 2010).

Ashkenasy et al., "Recognizing a Single Base in an Individual DNA Strand: A Step Toward Nanopore DNA Sequencing", Angew Chem Int Ed Engl., vol. 44, No. 9, pp. 1401-1404, Feb. 2005.

Butler et al., "Single-molecule DNA detection with an engineered MspA protein nanopore", PNAS, vol. 105, No. 52, pp. 20647-20652, Dec. 2008.

Cheley et al., "Stochastic Sensing of Nanomolar Inositol 1,4,5-Trisphosphate with an Engineered Pore", Chemistry and Biology, vol. 9, pp. 829-838, Jul. 2002.

Howorka et al., "Probing Distance and Electrical Potential within a Protein Pore with Tethered DNA", Biophysical Journal, vol. 83, No. 6, pp. 3202-3210, Dec. 2002.

Kasianowicz et al., "Characterization of individual polynucleotide molecules using a membrane channel", Proc. Natl. Acad. Sci. USA, vol. 93, pp. 13770-13773, Nov. 1996.

Sauer-Budge et al., "Unzipping Kinetics of Double-Stranded DNA in a Nanopore", Physical Review Letters, vol. 90, No. 23, pp. 238101-(1-4), Jun. 2003.

Vercoutere et al., "Discrimination among individual Watson-Crick base pairs at the termini of single DNA hairpin molecules", Nucleic Acids Research, vol. 31, No. 4, pp. 1311-1318, 2003.

* cited by examiner

Reporter Contructs

| | Duplex | Reporter |
|---|---|---|
| A0 Reporter | | |
| D2 | •••JCGGGC<br>　　$AGCCKG | DDDDDD••• |
| D3 | ••• JAGCGA<br>　　　ATKGKT | DDDDDD••• |
| D4 | •••JCGGGC<br>　　$ATCGKT | DDDDDD••• |
| A2 Reporter | | |
| D2 | •••JCGGGC<br>　　$AGCCKG | AADDDDD••• |
| D3 | ••• JAGCGA<br>　　　ATKGKT | AADDDDD••• |
| D4 | •••JCGGGC<br>　　$ATCGKT | AADDDDD••• |
| A4 Reporter | | |
| D1 | •••JCGGGC<br>　　$AGKCKG | AADAADDD••• |
| D3 | ••• JAGCGA<br>　　　ATKGKT | AADAADDD••• |
| A6 Reporter | | |
| D1 | •••JCGGGC<br>　　$AGKCKG | AAADAAADDDD••• |
| D3 | ••• JAGCGA<br>　　　ATKGKT | AAADAAADDDD••• |

Key:　K:　　G-clamp
　　　　$:　　3'-C3PT-NH2
　　　　J:　　dT-C6-NH2
　　　　D:　　PEG-6
　　　A,C,G,T canonical nucleotides.

*FIG. 4*

TRANSLOCATION CONTROL FOR SENSING BY A NANOPORE

BACKGROUND

Statement Regarding Sequence Listing

The Sequence Listing associated with this application is provided in text format in lieu of a paper copy, and is hereby incorporated by reference into the specification. The name of the text file containing the Sequence Listing is SEQUENCE_ LISTING.txt. The text file is 1.2 KB, was created on Aug. 15, 2019, and is being submitted electronically via EFS-Web.

Technical Field

This invention is generally directed to controlling the translocation of a target molecule for sensing by a nanopore, as well as methods and products relating to the same.

Description of the Related Art

Measurement of biomolecules is a foundation of modern medicine and is broadly used in medical research, and more specifically in diagnostics and therapy, as well in drug development. Nucleic acids encode the necessary information for living things to function and reproduce, and are essentially a blueprint for life. Determining such blueprints is useful in pure research as well as in applied sciences. In medicine, sequencing can be used for diagnosis and to develop treatments for a variety of pathologies, including cancer, heart disease, autoimmune disorders, multiple sclerosis, and obesity. In industry, sequencing can be used to design improved enzymatic processes or synthetic organisms. In biology, this tool can be used to study the health of ecosystems, for example, and thus has a broad range of utility. Similarly, measurement of proteins and other biomolecules has provided markers and understanding of disease and pathogenic propagation.

An individual's unique DNA sequence provides valuable information concerning their susceptibility to certain diseases. It also provides patients with the opportunity to screen for early detection and/or to receive preventative treatment. Furthermore, given a patient's individual blueprint, clinicians will be able to administer personalized therapy to maximize drug efficacy and/or to minimize the risk of an adverse drug response. Similarly, determining the blueprint of pathogenic organisms can lead to new treatments for infectious diseases and more robust pathogen surveillance. Low cost, whole genome DNA sequencing will provide the foundation for modern medicine. To achieve this goal, sequencing technologies must continue to advance with respect to throughput, accuracy, and read length.

Over the last decade, a multitude of next generation DNA sequencing technologies have become commercially available and have dramatically reduced the cost of sequencing whole genomes. These include sequencing by synthesis ("SBS") platforms (Illumina, Inc., 454 Life Sciences, Ion Torrent, Pacific Biosciences) and analogous ligation based platforms (Complete Genomics, Life Technologies Corporation). A number of other technologies are being developed that utilize a wide variety of sample processing and detection methods. For example, GnuBio, Inc. (Cambridge, Mass.) uses picoliter reaction vessels to control millions of discreet probe sequencing reactions, whereas Halcyon Molecular (Redwood City, Calif.) was attempting to develop technology for direct DNA measurement using a transmission electron microscope.

Nanopore based nucleic acid sequencing is a compelling approach that has been widely studied. Kasianowicz et al. (Proc. Natl. Acad. Sci. USA 93: 13770-13773, 1996) characterized single-stranded polynucleotides as they were electrically translocated through an alpha hemolysin nanopore embedded in a lipid bilayer. It was demonstrated that during polynucleotide translocation partial blockage of the nanopore aperture could be measured as a decrease in ionic current. Polynucleotide sequencing in nanopores, however, is burdened by having to resolve tightly spaced bases (0.34 nm) with small signal differences immersed in significant background noise. The measurement challenge of single base resolution in a nanopore is made more demanding due to the rapid translocation rates observed for polynucleotides, which are typically on the order of 1 base per microsecond. Translocation speed can be reduced by adjusting run parameters such as voltage, salt composition, pH, temperature, and viscosity, to name a few. However, such adjustments have been unable to reduce translocation speed to a level that allows for single base resolution.

Stratos Genomics has developed a method called Sequencing by Expansion ("SBX") that uses a biochemical process to transcribe the sequence of DNA onto a measurable polymer called an "Xpandomer" (Kokoris et al., U.S. Pat. No. 7,939,259, "High Throughput Nucleic Acid Sequencing by Expansion"). The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing detection technologies and are well suited to nanopore sequencing.

Gundlach et al. (Proc. Natl. Acad. Sci. 107(37): 16060-16065, 2010) have demonstrated a method of sequencing DNA that uses a low noise nanopore derived from *Mycobacterium smegmatis* ("MspA") in conjunction with a process called duplex interrupted sequencing. In short, a double strand duplex is used to temporarily hold the single stranded portion in the MspA constriction. This process enables better statistical sampling of the bases held in the limiting aperture. Under such conditions single base identification was demonstrated; however, this approach requires DNA conversion methods such as those disclosed by Kokoris et al. (supra).

Akeson et al. (WO2006/028508) disclosed methods for characterizing polynucleotides in a nanopore that utilize an adjacently positioned molecular motor to control the translocation rate of the polynucleotide through or adjacent to the nanopore aperture. At this controlled translocation rate (350-2000 Hz (implied measurement rate)), the signal corresponding to the movement of the target polynucleotide with respect to the nanopore aperture can be more closely correlated to the identity of the bases within and proximal to the aperture constriction. Even with molecular motor control of polynucleotide translocation rate through a nanopore, single base measurement resolution is still limited to the dimension and composition of the aperture constriction. As such, in separate work, Bayley et al. (alpha hemolysin: Chemistry & Biology 9(7):829-838, 2002) and Gundlach et al. (MspA: Proceedings of the National Academy of Sciences 105(52): 20647-20652, 2008) have disclosed methods for engineering nanopores with enhanced noise and base resolution characteristics. However, a demonstration of processive individual nucleotide sequencing has yet to be published that uses either (or both) a molecular motor for translocation control and an engineered nanopore. Current state of the art suggests that signal deconvolution of at least triplet base sets would be required in order to assign single base identity.

Nanopores have proven to be powerful amplifiers, much like their highly exploited predecessors, Coulter Counters. However, the current generation of organic nanopores (such as Hemolysin and MspA), that have been tasked with base recognition of DNA, are transmembrane proteins that do not interact with DNA in nature. They do not have natural functions for controlling DNA translocation. As has been discussed, this is a recognized shortcoming that some have attempted to correct by adding functionality with protein motors adjacent to the nanopores. For example, Akeson's group added phi 29 polymerase adjacent to the alpha-hemolysin nanopore so that ss-DNA could be fed into the pore at a controlled rate (see G. M. Cherf et al. "Automated forward and reverse ratcheting of DNA in a nanopore at 5-A precision," Nat Biotech, vol. advance online publication, February 2012). This approach complicates the assay and imposes a separation of the measurement region in the alpha hemolysin from the position control in the polymerase that can introduce additional noise and sequence dependent variation to the measurement.

Translocation control by hybridization (TCH) is used herein to refer to a method to pause a nanopore translocation event by using a structure created by hybridization which disassociates for translocation to proceed. Akeson et al. (U.S. Pat. No. 6,465,193) first demonstrated this by pausing DNA translocation with sequential hairpin duplexed regions. Translocation stopped at the duplex because it was larger than the α-hemolysin nanopore aperture. When the duplex released due to stochastic thermal fluctuation, translocation proceeded to the next duplex. During each pause, the region of DNA located in the nanopore (adjacent to the duplex) could be measured and identified. Akeson measured translocations of molecules with sequential duplexed regions and identified homogeneous regions adjacent to the duplexes. He estimated the mean of the stochastic pauses to be 15 to 18 µs per base pair for hairpin duplexes of 2 to 10 base pairs. Akeson further proposed that similar methods of pausing could be accomplished with alternative non-DNA structures.

Meller et al. (U.S. Pat. No. 7,972,858) used TCH to sequentially pause the translocation of the DNA with a series of duplexes formed by hybridizing complimentary oligomers to regions along the DNA. This technique utilized an optical technique to measure the each type of duplex that was sequentially released.

Gundlach et al. also used complementary oligomers for TCH (which he called "duplex interrupted") to measure DNA designed with multiple duplex regions using a low noise nanopore derived from *Mycobacterium smegmatis* ("MspA") (Proc. Natl. Acad. Sci., 2010). In this case the duplexes were formed by free strand hybridization and paused an adjacent 3-base homopolymer portion in the MspA constriction for measurement. Under such conditions three-base homopolymer identification was demonstrated. The complementary oligomers used for duplexing were 14 bases long, but had poor hybridization fill rates of only 65%. For sequencing, this approach requires DNA conversion methods such as those disclosed by Kokoris et al. or Meller et al. (supra).

In addition, groups have previously used duplexes to hold and release molecules form nanopores for a variety of applications, for example: (i) F. Sauer-Budge et.al., "Unzipping Kinetics of Double-Stranded DNA in a Nanopore," Phys. Rev. Lett., vol. 90, no. 23, p. 238101, June 2003; (ii) N. Ashkenasy, J. Sánchez-Quesada, M. R. Ghadiri, and H. Bayley, "Recognizing a Single Base in an Individual DNA Strand: A Step Toward Nanopore DNA Sequencing," Angew Chem Int Ed Engl, vol. 44, no. 9, pp. 1401-1404, February 2005; (iii) S. Howorka and H. Bayley, "Probing Distance and Electrical Potential within a Protein Pore with Tethered DNA," Biophysical Journal, vol. 83, no. 6, pp. 3202-3210, December 2002; and (iv) W. A. Vercoutere, S. Winters-Hilt, V. S. DeGuzman, D. Deamer, S. E. Ridino, J. T. Rodgers, H. E. Olsen, A. Marziali, and M. Akeson, "Discrimination among individual Watson-Crick base pairs at the termini of single DNA hairpin molecules," Nucleic Acids Res, vol. 31, no. 4, pp. 1311-8, February 2003.

While significant advances have been made in this field, commercially viable implementation of duplex translocation control with, for example, Xpandomers would benefit from improvements that overcome limitations caused by duplexing, including: (i) compositions for reporters to provide low noise, ion current blockage signals with amplitudes distributed for distinct high signal-to-noise measurements in nanopores; (ii) compositions that provide for uniform TCH release rates; (iii) improving poor hybridization fill rate on Xpandomer TCH duplex sites (ideally approaching 100% since each missed duplex can lead to lost sequence information); (iv) improving or mitigating lost dynamic range due to ion current blockage of the duplex at the nanopore entrance; and/or (v) methods to better utilize nanopore measurement bandwidth that is limited by the stochastics of duplex dissociation.

The present invention fulfills these needs and provides further related advantages as discussed below.

BRIEF SUMMARY

In brief, methods are disclosed for controlling the translocation of a target molecule for sensing by a nanopore, as well as to products relating to the same.

In one embodiment, methods are disclosed that optimize duplex stability to provide high fill rate (of the hybridization sites) on the Xpandomer but do not prevent rapid dissociation required for high read rates.

In another embodiment, a duplex is provided that increases the dynamic range by reducing the ionic current impedance due to the duplex blockage of the nanopore.

In a further embodiment, the complementary regions of the duplexes are reduced to 5 to 8 base pairs by using G-clamp nucleotide analogs to increase stabilization reducing Xpandomer length for improved performance and reduced costs.

In another embodiment, dissociation rate of the duplexes is controlled by a voltage control technique. This technique increases the sequence measurement rate for a given bandwidth by enabling regular clocking of the dissociation release overcoming limitations of the stochastic dissociation under constant voltage measurements. In addition, the predictable release time removes temporal uncertainty of a transition and simplifies signal analysis methods.

In another embodiment, a method for controlling the translocation of a target molecule for sensing by a nanopore is disclosed, the method comprising passing the target molecule through the nanopore subjected to a base voltage and a pulsed voltage, wherein the target molecule comprises two or more duplex features which provide translocation control by hybridization. In a more specific aspect of this embodiment, the pulsed voltage is sufficient to release the duplex feature engaged with the nanopore, while leaving the next duplex feature of the target molecule to engage with the nanopore unaffected.

In more specific embodiments, the pulsed voltage has a duration of less than 100 microseconds, less than 50 microseconds, less than 10 microseconds, less than 5 microseconds, or less than 1 microseconds In more specific embodiments, the pulsed voltage has a voltage of greater than 0.2 volts, greater than 0.5 volts, greater than 1 volt, or greater than 10 volts.

In more specific embodiments, the periodicity of the pulsed voltage ranges from 50 Hz to 10 kiloHz.

In more specific embodiments, the target molecule is sensed by the nanopore during the time period between pulses of the pulsed voltage.

In more specific embodiments, a duplex feature of the target molecule is released upon each pulse of the pulsed voltage, and in another embodiment is released upon multiple pulses of the pulsed voltage.

In another embodiment, a reporter construct is disclosed comprising a low impedance polymer and a high impedance polymer. Exemplary low impedance polymers include triethylene glycol (X), hexaethylene glycol (D), ethane (L), hexane (P), dodecane (Z), and abasic (Q), while exemplary high impedance polymers include deoxyadenosine (A), deoxythymine (T), deoxycytosine (C), and deoxyguanosine (G).

In a further embodiment, a reporter construct is disclosed comprising two or more phosphoramidites selected from the group consisting of triethylene glycol (X), hexaethylene glycol (D), ethane (L), hexane (P), dodecane (Z), deoxyadenosine (A), deoxythymine (T), deoxycytosine (C), deoxyguanodine (G) and abasic (Q), and wherein the reporting construct comprises at least one of X, D, L, P, Z or Q.

In another embodiment, at least a reporter may comprise the backbone with an additional chemical conjugate that can cause deeper ion current blockage states. This may be a base-conjugation or may result from a branched phosphoramidite.

These and other aspects of the invention will be apparent upon reference to the following detailed description. To this end, various references are set forth herein which describe in more detail certain background information, procedures and/or products, and are each hereby incorporated by reference in their entirety.

BRIEF DESCRIPTION OF THE SEVERAL VIEWS OF THE DRAWINGS

FIG. 4 depicts representative structures for reporters along with several types of duplexes.

DETAILED DESCRIPTION

Figure 1:
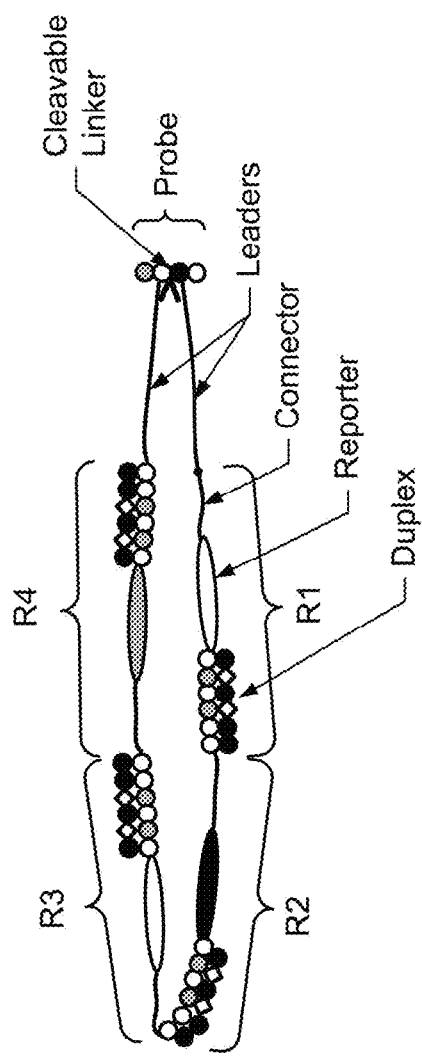
FIG. 1 depicts a representative Xprobe having a 4-base probe with base sequence information encoded in 4 reporter constructs labeled R1, R2, R3, and R4 located along the tether representative Xprobe.
Figure 2:
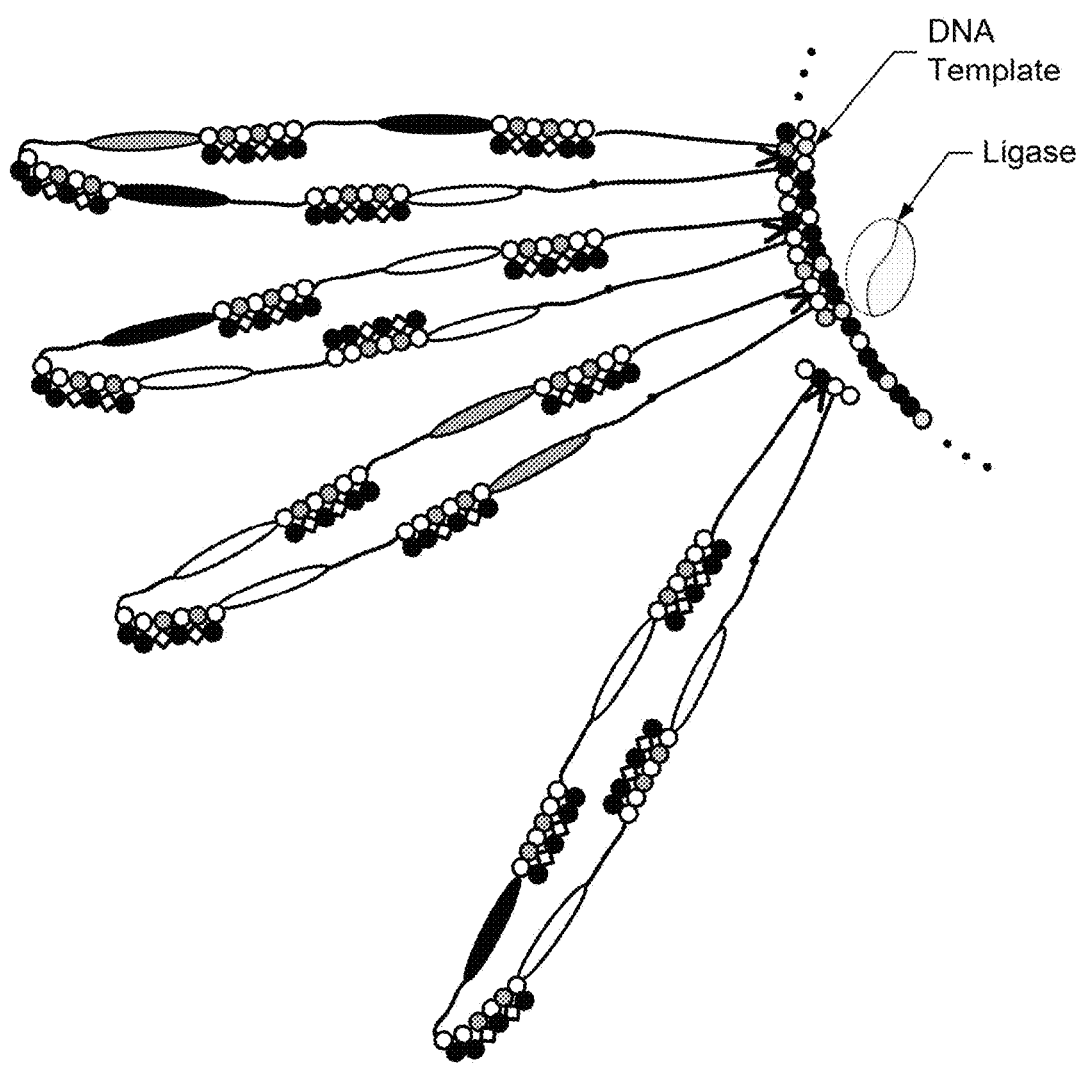
FIG. 2 depicts how representative sequence-specific Xprobes are ligated by template dependent extension to the template target and form an Xpandomer.

Sequencing by expansion (SBX) encodes base sequence information into reporters that are positioned on the tethers of specialized SBX probes called Xprobes (Kokoris et al). FIG. 1 shows a Xprobe with a 4-base probe with base sequence information encoded in 4 reporter constructs labeled R1, R2, R3, and R4 located along the tether. FIG. 2 shows how the sequence-specific Xprobes are ligated by template dependent extension to the DNA template target and form the Xpandomer. Through synthesis of the Xpandomer, the DNA sequence is now encoded along the tether in the ordering of the reporter constructs.

The Xprobe depicted in FIG. 1 has a tether designed for translocation control by hybridization (TCH). As depicted, each reporter construct (R1, R2, R3 and R4) has a region of hybridization which can be duplexed to a complementary oligomer (CO) and is positioned adjacent to a reporter. Following the reporter is a connector portion that provides a spacer before the next reporter construct begins. Also shown in this figure is the cleavable linker located between the probe bases with tether attachment points. After the Xpandomer is synthesized, this linker is cleaved under specific conditions which allow the tether to elongate.

Another method of Xpandomer synthesis uses an X-NTP (Kokoris et al.) rather than an Xprobe to extend the template-dependent synthesis and uses polymerase rather than ligase as a catalyst. This method has the advantage of using a small library of 4 X-NTP relative to a much larger Xprobe library (4N where the Xprobe is an N-mer).

Figure 3:
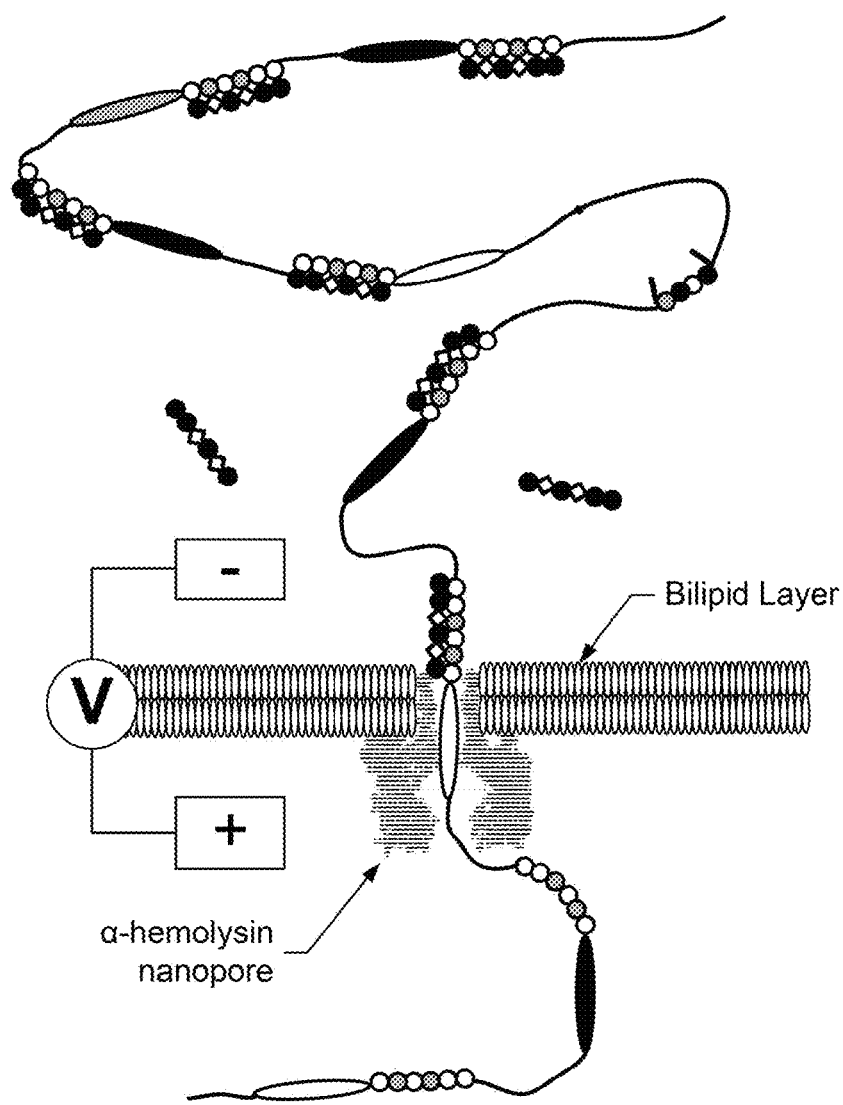
FIG. 3 depicts a representative cleaved Xpandomer in the process of translocating an α-hemolysin nanopore.

FIG. 3 shows a cleaved Xpandomer in the process of translocating an α-hemolysin nanopore. This biological nanopore is embedded into a lipid bilayer membrane which separates and electrically isolates two reservoirs of electrolytes. A typical electrolyte has 1 molar KCl buffered to a pH of 7.0. When a small voltage, typically 100 mV, is applied across the bilayer, the nanopore constricts the flow of ion current and is the primary resistance in the circuit. Xpandomer reporters are designed to give specific ion current blockage levels and sequence information can be read by measuring the sequence of ion current levels as the sequence of reporters translocate the nanopore.

A wild-type α-hemolysin nanopore can be described by 2 structural volumes along its axis, the vestibule which is 2.8 nm across at its entrance and widens to 4.8 nm before converging to a 1.5 nm "pinch" point that marks the start of the 2nd volume called the stem. The stem is more cylindrical, ranging from 1.5 nm to 2.6 nm but constricts to 2.2 nm at its exit (L. Song, M. R. Hobaugh, C. Shustak, S. Cheley, H. Bayley, and J. E. Gouaux, "Structure of staphylococcal alpha-hemolysin, a heptameric transmembrane pore," Science, vol. 274, no. 5294, pp. 1859-1866, December 1996).

The α-hemolysin nanopore is typically oriented so translocation occurs by entering the vestibule side and exiting the stem side. As shown in FIG. 3, the nanopore is oriented to capture the Xpandomer from the stem side first. This orientation is advantageous using the TCH method because it causes fewer blockage artifacts that occur when entering vestibule first. Unless indicated otherwise, stem side first will be the assumed translocation direction.

As the Xpandomer translocates, a reporter enters the stem until its duplex stops at the stem entrance. The duplex is ~2.4 nm in diameter whereas the stem entrance is ~2.2 nm so the reporter is held in the stem until the complimentary strand of the duplex disassociates (releases) whereupon translocation proceeds to the next reporter. The free complementary strand is highly disfavored from entering the nanopore because the Xpandomer is still translocating and diffuses away from the pore.

Nanopores may be broadly classified into biological and synthetic types, and both types are intended to be within the scope of this invention. While alpha hemolysin (αHL) is perhaps the most studied biological nanopore to date, this and other biological nanopores may be utilized in the context of this invention, such as *Mycobacterium smegmatis* porin A (MspA). More recently, synthetic nanopores have been introduced using polymers, aluminum oxide, silicon dioxide, silicon nitride or other thin solid-state membranes. A requirement to use TCH on any nanopore is that diameter be restricted at least one point so the duplexed region of the reporter construct will be stopped until the duplex releases. All such design options are within the scope of this invention.

Each reporter construct uses its duplex to position its reporter within a zone of the nanopore that has high ion current resistance. In alpha hemolysin, this zone is the stem. In this zone, different reporters are sized to block ion flow at different measurable levels. Specific reporters can be efficiently synthesized using phosphoramidite chemistry typically used for oligonucleotide synthesis. Reporters can be designed by selecting a sequence of specific phosphoramidites from commercially available libraries. Such libraries include but are not limited to polyethylene glycol with lengths of 1 to 12 or more ethylene glycol units, aliphatic with lengths of 1 to 12 or more carbon units, deoxyadenosine (A), deoxycytosine (C), deoxyguanodine (G), deoxythymine (T), abasic (Q). Table 1 below lists some representative phosphoramidites.

TABLE 1

Representative Phosphoramidites

| Phosphoramidite | Short Name | Symbol |
|---|---|---|
| Triethylene glycol | PEG-3 | X |
| Hexaethylene glycol | PEG-6 | D |
| Ethane | C-2 | L |
| Hexane | C-6 | P |
| Dodecane | C-12 | Z |
| Deoxyadenosine | dA | A |
| Deoxythymine | dT | T |
| Deoxycytosine | dC | C |
| Deoxyguanosine | dG | G |
| Abasic | ab | Q |
| Spermine | Sp | S |

Reporter design is guided by balancing measurement characteristics including: (i) normalized ion current ($I/I_o$): where I is ion current and $I_o$ is the open channel current; (ii) ion current noise: includes multi-state responses, blockages, random spiking, and the like; and/or (iii) release time of the duplex.

Reporter ion current blockage and its duplex release time is also modulated by measurement conditions such as: (i) voltage; (ii) electrolyte; (iii) temperature; (iv) pressure; and/or (v) pH.

The duplex associated with the reporter also contributes to the ion current blockage.

For a given set of measurement conditions reporters can be designed for a minimum and maximum I/Io levels that define the measurement dynamic range. Other reporters can be designed with different I/Io levels within the dynamic range. As each reporter is paused in the nanopore, the measured I/Io level must remain stationary long enough and have low enough noise that the reporter type can be uniquely distinguished.

The maximum I/Io level reporter would ideally have a duplex that blocks minimally followed by a reporter with thin nonblocking cross-section. In contrast, the minimum I/Io level approaches full blockage with a large cross-section backbone (and optionally a deep blocking duplex). An additional requirement is that the reporter clears the pore with relative ease after the duplex dissociates. It is noteworthy that the blockage is due to a composite resistance formed along the narrower portions of the nanopore channel.

In one embodiment, each member of a reporter set (following the duplex) is formed by an ordered choice of phosphoramidites that can be selected from many commercial libraries. Each constituent phosphoramidite contributes to the net ion resistance according to its position in the nanopore (located after the duplex stop), its displacement, its charge, its interaction with the nanopore, its chemical and thermal environment and other factors. The charge on each phosphoramidite is due, in part, to the phosphate ion which has a nominal charge of −1 but is effectively reduced by counterion shielding. The force pulling on the duplex is due to these effective charges along the reporter which are acted upon by the local electric fields. Since each reporter can have a different charge distribution, it can exert a different force on the duplex for a given applied voltage. The force transmitted along the reporter backbone also serves to stretch the reporter out to give a repeatable blocking response.

In this example, reporters were designed by choosing phosphoramidite building blocks from deoxyadenosine (dA) and hexaethylene glycol (PEG-6) (ChemGenes, MA)). Four reporters were designed by adding 0, 2, 4, and 6 dA in series with the PEG-6 backbone (referred to as 0 A, 2 A, 4 A and 6 A respectively). The poly-dA portion is after the duplex so the reporter is positioned in the alpha-hemolysin stem when the duplex stops at the stem entrance. FIG. 4 shows the structure of the 4 reporters along with several types of duplexes. For the A4 and A6 reporter the poly-dA portions are AADAA and AAADAAA respectively where a PEG-6 (indicated as D) is placed to tune the ion blocking level response.

The reporter with the maximum I/Io response has 6 PEG-6 phosphoramidites in series. Each PEG-6 had a contour length of ~1.95 nm including its phosphodiester linkage, so the reporter had a total contour of 11.7 nm, longer than the alpha-hemolysin pore channel of ~10 nm. The additional length means that the previous reporter's duplex site can translocate beyond the vestibule and minimize any further interaction with the nanopore. In a similar manner the reporters with poly-dA portions have an additional poly-PEG-6 segment to provide vestibule clearance.

Dissociation (or release) of the duplex is a thermal stochastic process that depends upon multiple factors, including: (i) constituent duplex pairing strengths and order; (ii) applied voltage; (iii) differential pressure; (iv) electrolyte; (v) temperature; and/or (vi) pH.

A viable sequencing method must have minimal information loss and for some applications require <$10^{-4}$ error rates. Individual reads, though, may have high raw error rates (e.g., ion torrent, MiSeq are ~1 in 300). By making many redundant measurements of a sequence region, the consensus of many individual reads can achieve the desired error rate. All errors are not equivalent due to the additional burden they have on information processing or discarded measurements. Insertions and deletions that cannot be localized can seriously degrade the data quality.

Since a missing duplex is a deletion error, efficient TCH sequencing requires conditions where duplex fill approaches 100%. Duplex fill is defined as the ratio of the number of duplexed reporter constructs to the total number of reporter constructs along the sampled Xpandomers. Short DNA oligomer duplexes of 7 to 8 bases (40 to 50% GC) have duplexing rates of kon ~1e7 $M^{-1}$ $s^{-1}$ at room temperature for 2M salt conditions (S. Howorka, et al. Proceedings of the National Academy of Sciences of the United States of America, vol. 98, no. 23, pp. 12996-13001, November 2001) and dissolution rates of koff ~1 $s^{-1}$. Thus for a duplex site to be duplexed 99% of the time requires that the kon*M/koff=99 where M is the duplex molarity. This yields a molarity requirement of M=99/1e7~10 μM.

Nucleic acid analogs with higher base pairing strengths can reduce the duplex length and increase stability to achieve high duplex fill. Some analogs that have demonstrated higher melt temperatures than the canonical DNA base pairs include 2'Methoxy RNA, 2'Fluoro RNA, PNA, LNA and RNA.

A variety of nucleotide modifications located either at the ends or internal to the oligomer can also be used to modify stability. For example a 3' amino end group helps to stabilize the duplex complement that approaches a nanopore from the 5' side.

Figure 5:
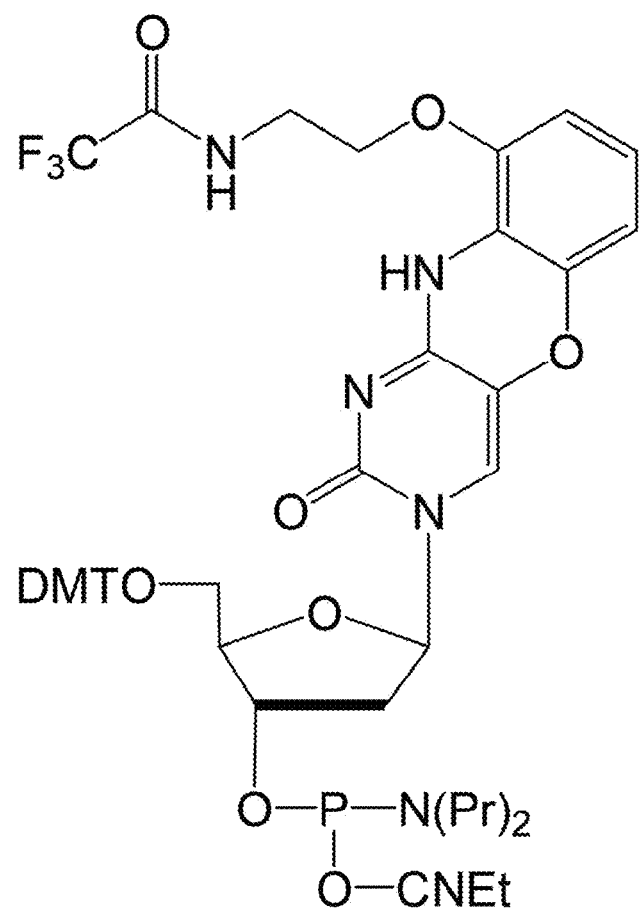
FIG. 5 depicts a representative G-clamp phosphoramidite that allows duplexes to be synthesized directly on a synthesizer with specific G-clamp incorporations.

G-clamps (Isis Pharmaceuticals) are Cytosine analogs that will selectively base-pair to Guanine and will raise thermal melt temperatures significantly. FIG. 5 shows a G-clamp phosphoramidite that allows duplexes to be synthesized directly on a synthesizer with specific G-clamp incorporations.

Figure 6A:
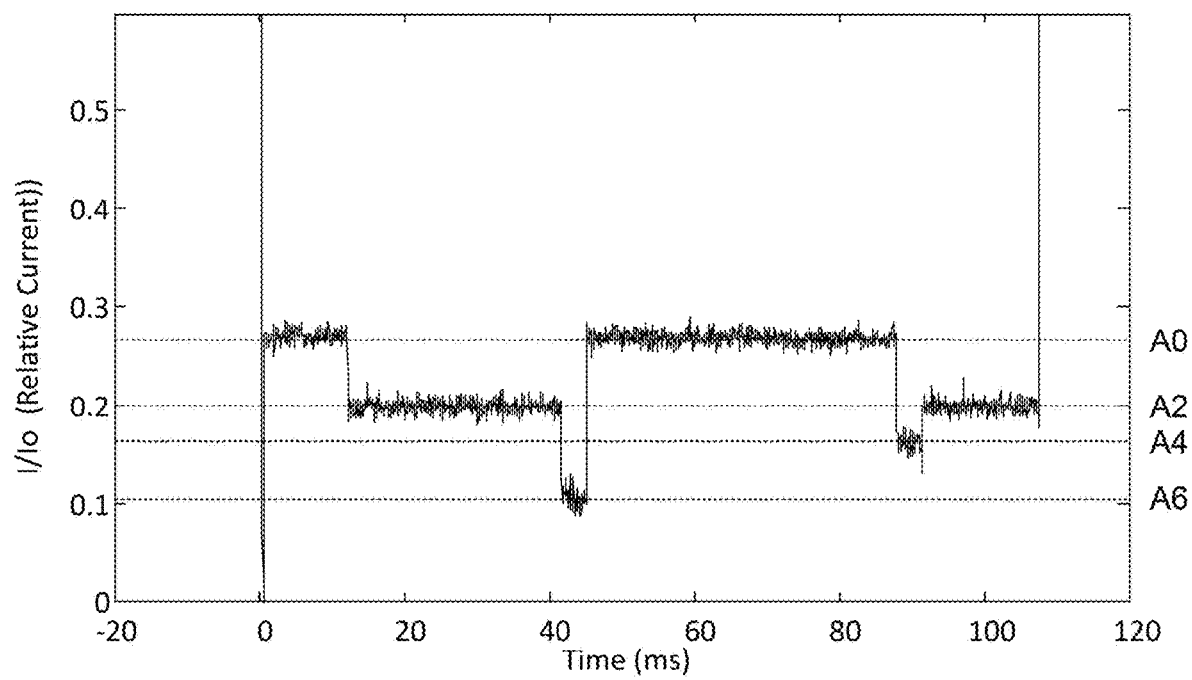
FIGS. 6A and 6B depicts two representative current traces of 6-reporter tether translocations.
Figure 6B:
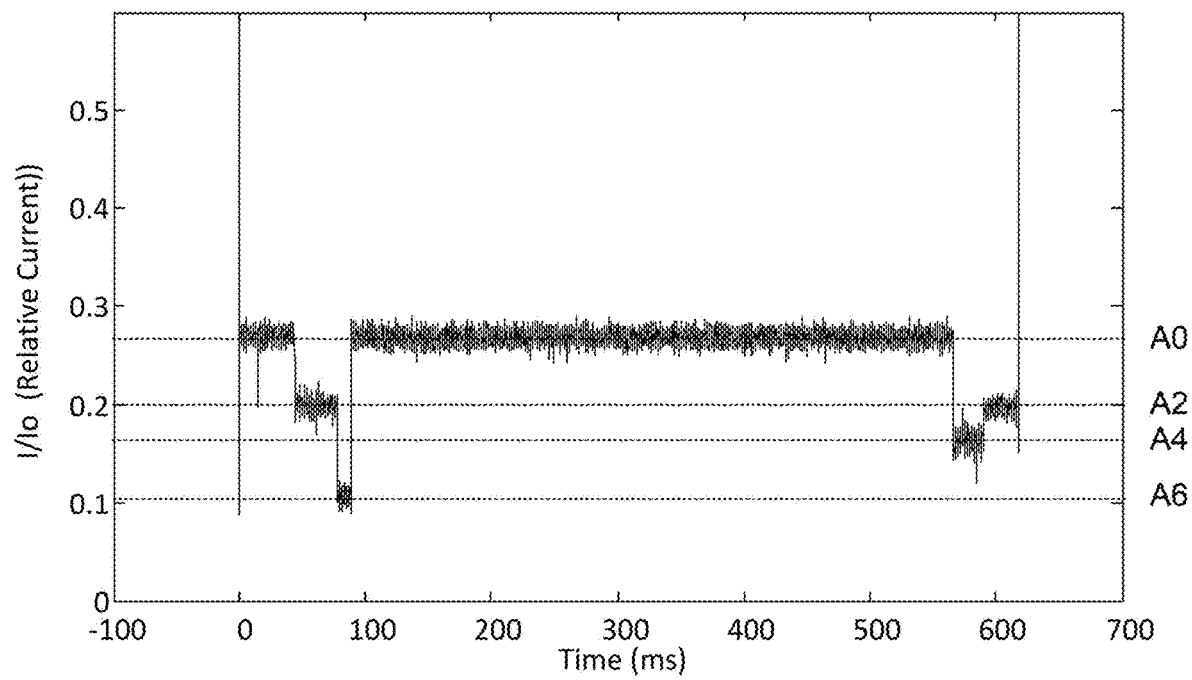
Figure 7A:
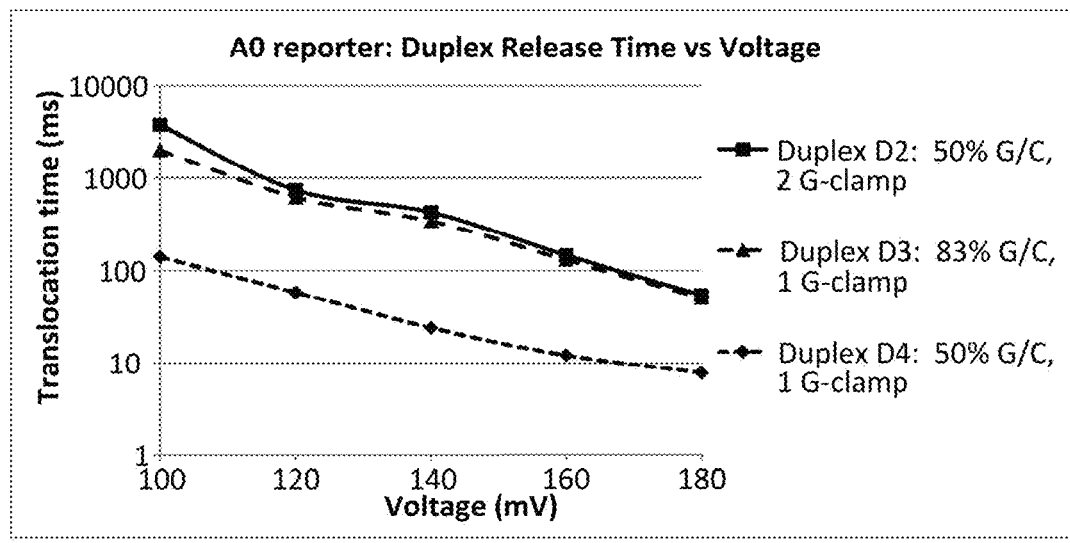
FIGS. 7A through 7D depicts average duplex release times for reporter constructs plotted as a function of potential applied across the nanopore.
Figure 7B:
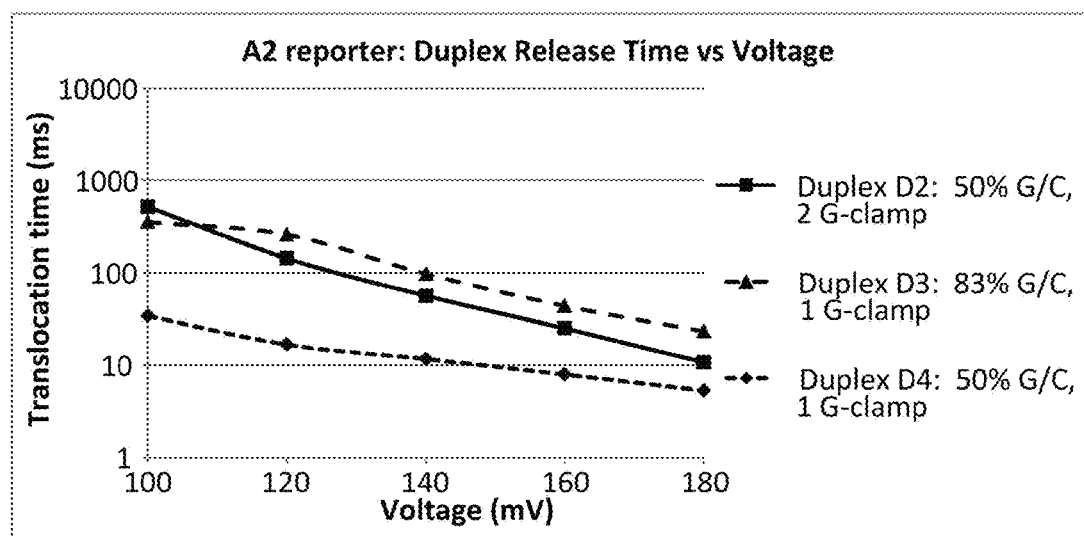
Figure 7C:
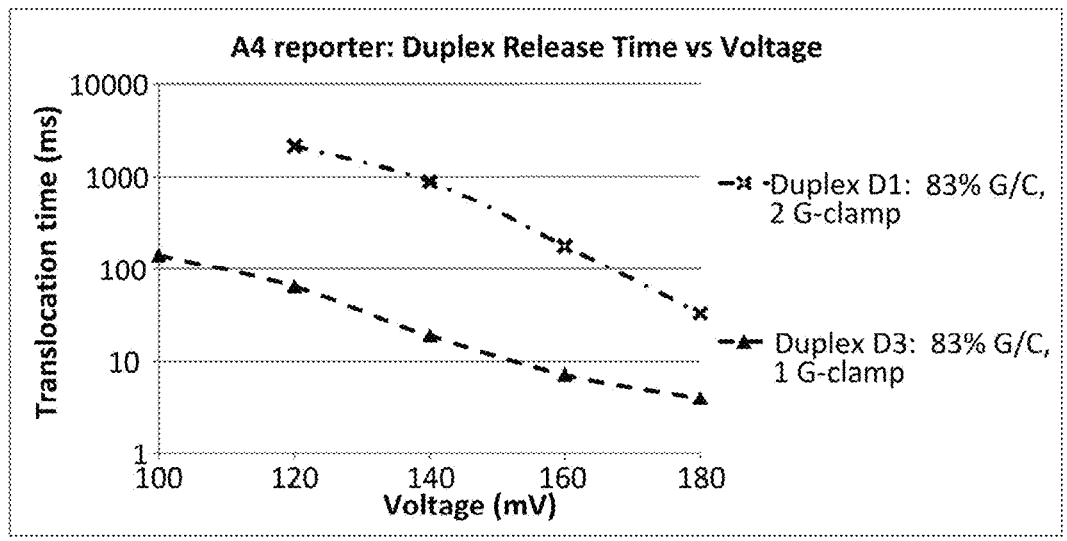
Figure 7D:
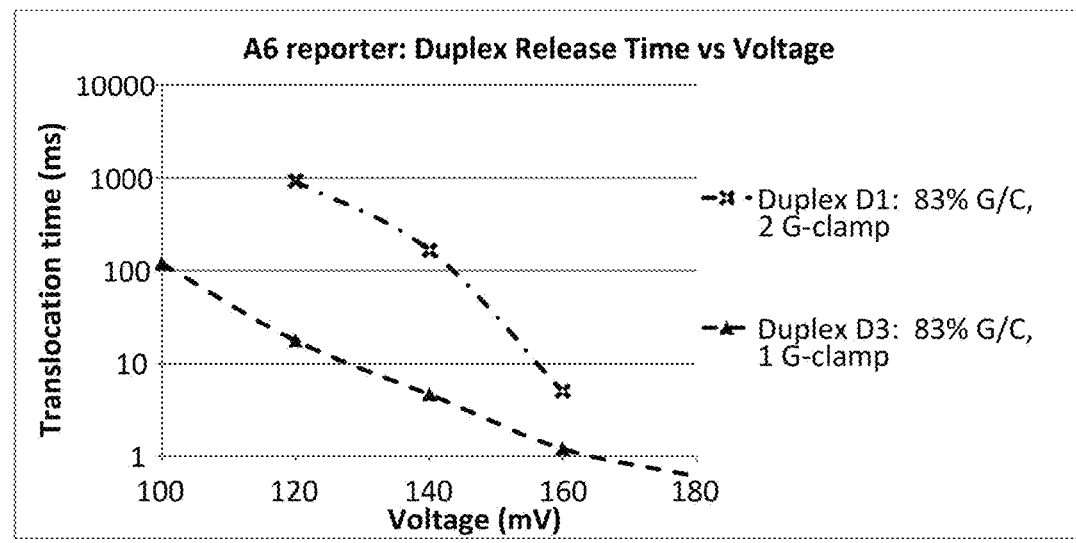

Replacing 1 or 2 cytosine bases with these G-clamps, in an otherwise canonical base duplex provides substantial increase in stability and free solution fill rates. FIG. 4 shows the composition of 4 different hexamer duplexes labeled D1, D2, D3, and D4 that are incorporated into reporter constructs. The constructs also incorporate 4 reporters A0, A2, A4 and A6. Six reporter constructs were synthesized into longer reporter tethers using phosphoramidite chemistry. The 4 reporters block ions in a hemolysin nanopore at 4 different levels. Increasing the number of adenosines in the nanopore stem increases the charge density, decreases the volume through which ions can diffuse, and results in increased ion current resistance. With nanopore buffer of 2 molar $NH_4Cl$/10 mM HEPES, pH 7.4, and temperature of 20 degrees C., data was logged. FIGS. 6A and 6B show two example current traces of 6-reporter tether translocations captured at 140 mV. The trace current is shown normalized to the open channel current which is 182 pA. The order of the six reporters on the tether is A0, A2, A4, A0, A3, A2. As the tether translocates, a duplex stops each reporter in the stem of the nanopore and gives a characteristic blockage level as shown on the trace. As indicated in the traces, the relative ion blockages of the four reporters A0, A2, A4, and A6 are 0.270, 0.197, 0.163 and 0.106, respectively. The duplex dissociation times for each reporter type have an exponential distribution.

The average duplex release time for each reporter construct is plotted as a function of potential applied across the nanopore in the 4 plots of FIGS. 7A through 7D. The duplex releases under shear force as it resists translocation of the backbone molecule through the nanopore under some applied voltage. The kinetics of this release has been modeled by the Evans-Kramer escape kinetics (E. Evans, Annual Review of Biophysics and Bimolecular Structure, vol. 30, no. 1, pp. 105-128, 2001.) which predicts that the axial shear force causes an exponential increase in the release rate. The force is generated by the electric field acting upon the effective charges of the reporter inside the nanopore and primarily located in the nanopore stem. Thus by increasing either the potential or the number of effective charges decreases the average release time of the duplex. Each reporter was synthesized in a construct with duplex D3 and release times are shown on the plots. The release times of this duplex for A0, A2, A4, and A6 at 140 mV are 340, 97, 20 and 7 ms showing the effect of increasing charge in the nanopore stem caused by increasing the number of phosphate ions (one for each adenosine base). The plots show relative stability of the duplexes. Duplexes D1 and D3 have 2 and 1 G-clamps respectively but are otherwise identical and comparing release times shows D1 to be more stable D3 with release times typically 10 times longer (see plots for reporters A4 and A6). Duplexes D3 and D4 each have 1 G-clamp but their G/C contents are 83% and 50% respectively. This also increases stability and release times are typically 10 times longer (see FIGS. 7A and 7B for plots of reporters A0 and A2, respectively).

Extrapolation of the duplex release time curves to 0 mV provides an estimate of koff from the inverse of the intercept. These koff values ranged from $0.3 \text{ s}^{-1}$ to $<0.001 \text{ s}^{-1}$, all slower and therefore more stable than the 7 or 8 canonical base oligomers described by Howorka that had koff $\sim 1 \text{ s}^{-1}$.

If duplex fill is not 100%, other coding techniques can be used to provide redundant measurement or error checking. Xpandomer reporter tethers can encode reporters to provide additional functionality that reduce errors.

Like other sequencing methods, nanopores have difficulty resolving homopolymers. There is no inherent signal that will separate the ion current level responses of two consecutive identical bases (or reporters) as they slip through the nanopore.

Xpandomers can encode sequence information along its tether that avoids the homopolymer problem. The dynamic range of the nanopore TCH blockage current can resolve 4 to 8 levels. In one coding embodiment, a blockage level (and the associated reporter) is assigned for each base type and a $5^{th}$ level is used between identical adjacent bases and also at the end of each Xprobe tether. This forces a transition to occur between any 2 states but can increase the number of reporters per Xprobe to a variable number. For example in a tetramer Xprobe, the number of reporters can vary from 5 to 8 reporters depending upon the number of homopolymers.

Figure 8:
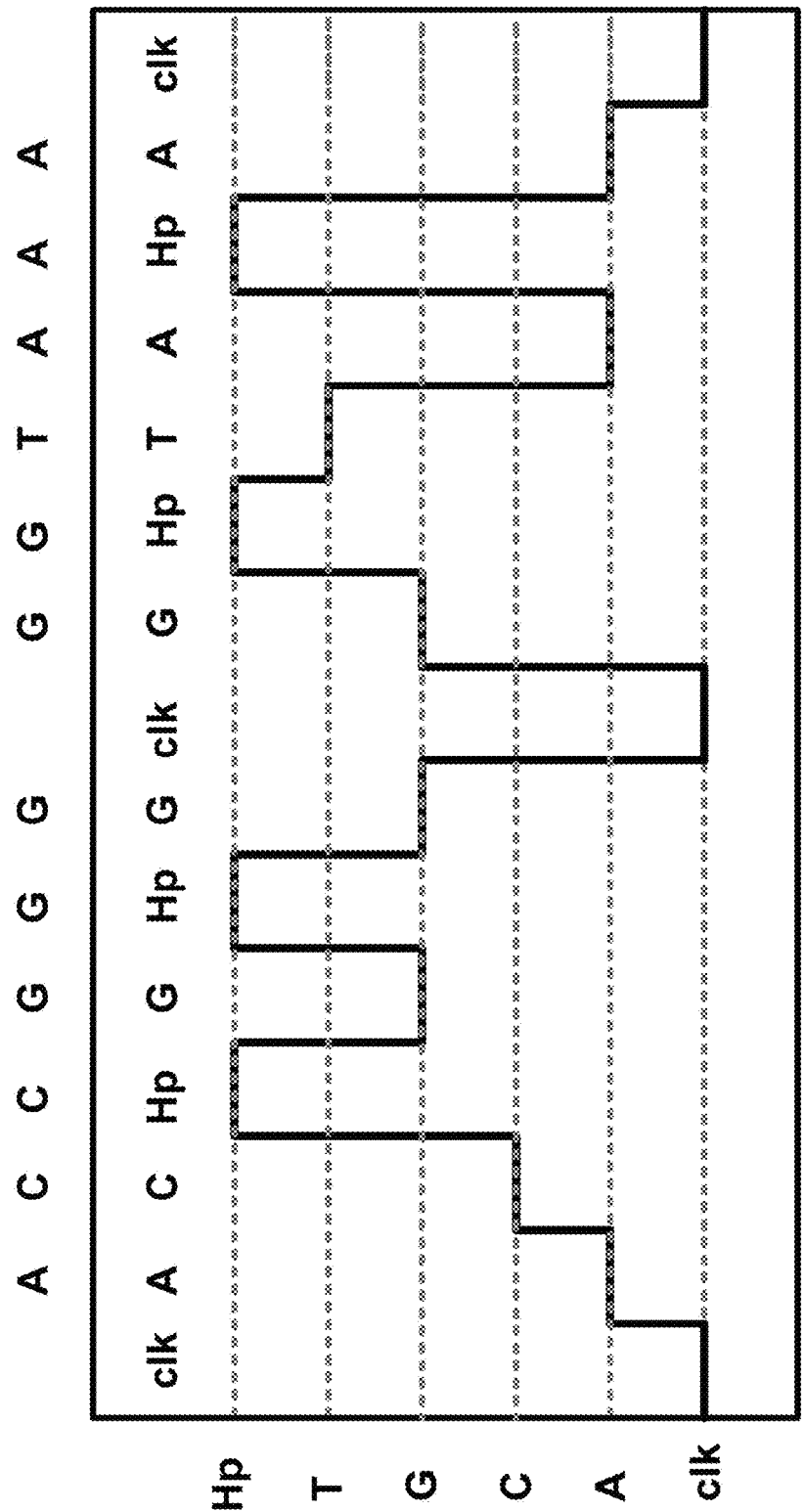
FIG. 8 depicts homopolymer encoding, with the base sequence for two hexamer Xprobes along the top of the figure and the encoded reporter levels shown beneath them.

Another embodiment is to assign a fifth ion blockage level to homopolymers (Hp). When there is a homopolymer sequence in the probe, it is encoded by assigning the correct base level reporter for the first base and then assigning the Hp reporter to the next. Any subsequent consecutive bases of the same type continue to switch between these two levels. To decode this, the base type for each Hp level measurement is determined by the previous base. FIG. 8 shows the base sequence for 2 hexamer Xprobes along the top. The encoded reporter levels are shown beneath them. An additional 6th ion blockage state called the clock (clk) level is added at the end of each Xprobe. This performs two functions. It provides an additional error check to inform the decoder that six levels should be read between clks and it resets the homopolymer coding between Xprobes. In this case five guanosine bases (G) fall across the two Xprobes. The clk level forces a transition between the third G at the end of the 1st Xprobe, and the first G of the second Xprobe.

In the case of the X-NTP synthesized Xpandomer, the tether only encodes for a single base. In one encoding scheme, a clock reporter is added to follow every base-type reporter to provide homopolymer discrimination.

An alternative method to TCH for slowing/stopping the reporter in the nanopore is to use steric hindrance of the reporter itself as it propagates through the nanopore. Mitchell conjugated an internal base of a 27-base DNA oligomer with different chemical tags and showed how these slowed the translocation times through a nanopore (Mitchell and Howorka, "Chemical Tags Facilitate the Sensing of Individual DNA Strands with Nanopores13," Angewandte Chemie International Edition, vol. 47, no. 30, pp. 5565-5568, 2008.) Mitchell claimed the TCH was constrained to a nanopore size range whereas the steric hindrance method could be adapted to larger sized pores. The steric hindrance reporters were shown to have deep ion current blockage states and may be used in conjunction with TCH to achieve deep states.

It is clear that other coding methods can be applied to reduce errors including cyclic redundancy codes that allow for 1 or more base call errors and still recover the correct information (Peterson, W. W. and Brown, D. T. (January 1961). "Cyclic Codes for Error Detection". *Proceedings of the IRE* 49(1): 228-235).

Figure 9:
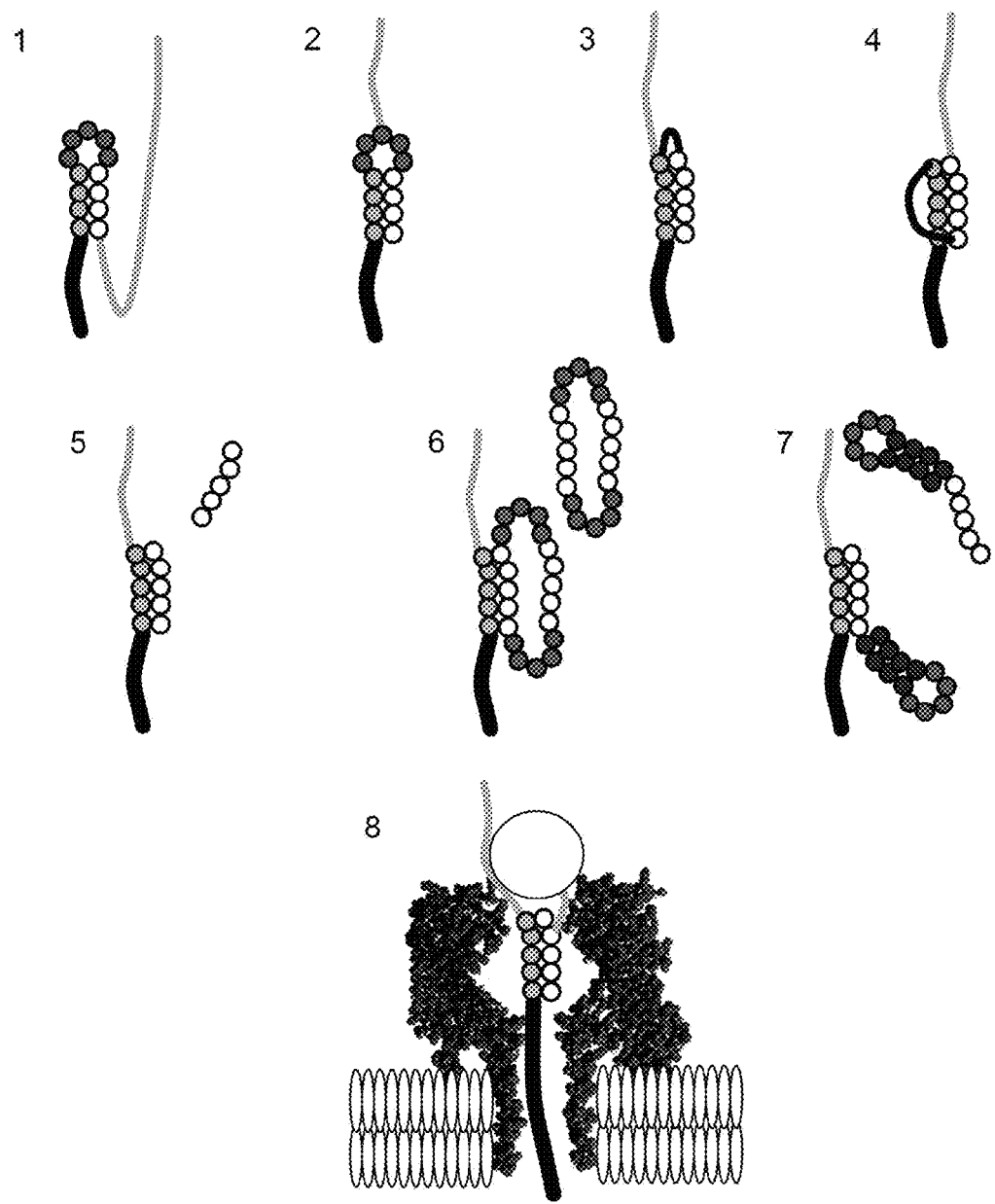
FIG. 9 depicts representative duplex designs.

The literature discusses two duplex designs that have been used for a TCH molecule; namely, referred to herein as the in-line hairpin and simple free duplex. These and other designs are shown in FIG. 9 and discussed individually below (the following numbers correspond to the designation numbers shown in FIG. 9).

(1) The "in-line hairpin" structure is so defined because the THC molecule's backbone (e.g., Xpandomer) passes through it. This structure, however, results in undesired blockages in an alpha-hemolysin during stem-first translocations, which is attributed to the hairpin causing the backbone to refold onto itself within the vestibule and not being able to exit.

Figure 10:
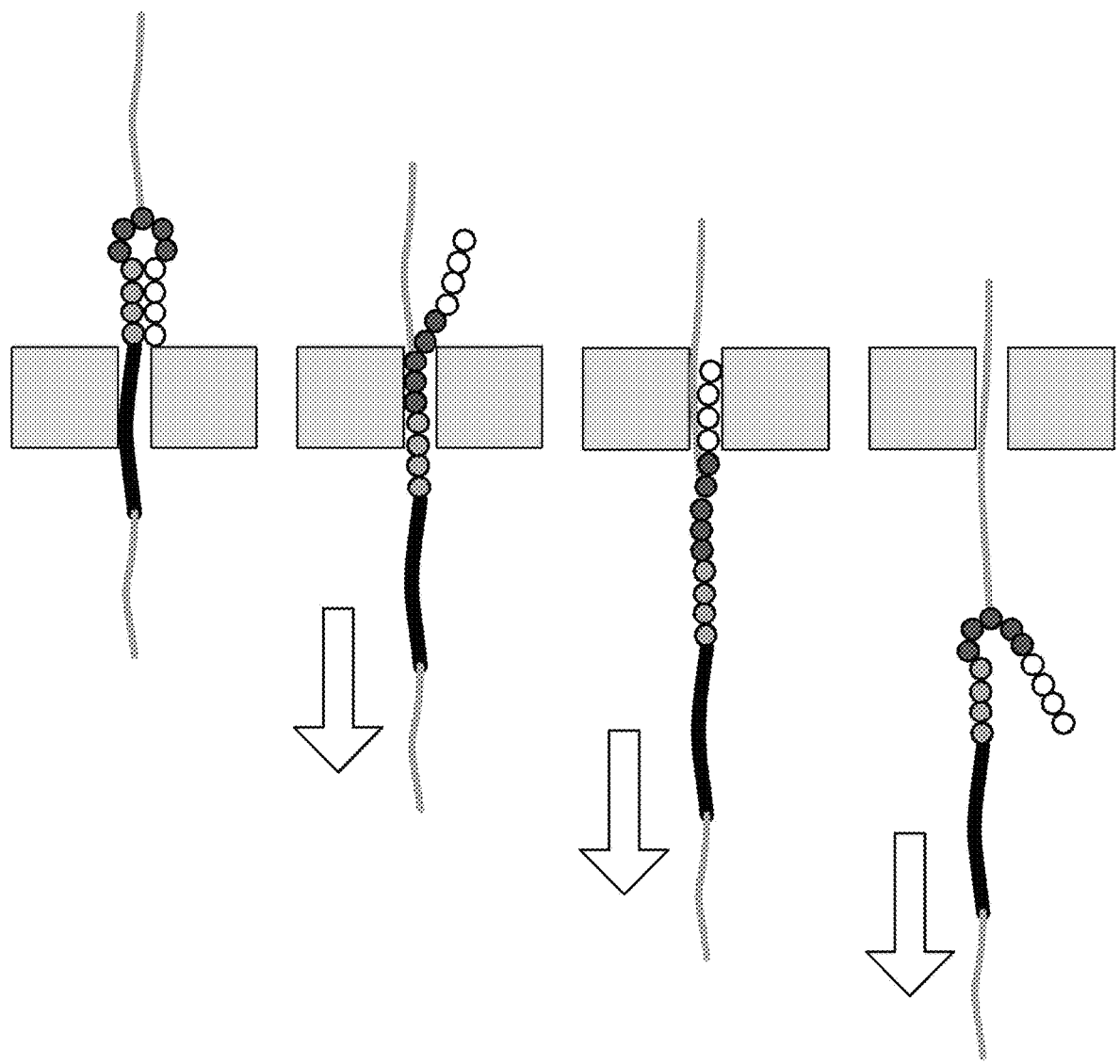
FIG. 10 depicts hairpin dissociation; namely (for left to right), in the translocation pause position, dissociation and folding back onto the trailing backbone, continuing to translocate the nanopore, and exiting the nanopore and beginning to refold.

(2) The "foldback hairpin" structure is a novel design that reduces entanglement and vestibule blockage issues by maintaining a linear orientation of the backbone. This is synthesized by branching the backbone at the loop midpoint using a pendant base conjugation to extend the backbone. In this case when the hairpin dissociates, it will unfold and align with the trailing backbone polymer that is sufficiently thin to allow continued translocation. FIG. 10 shows this progression in 4 steps, from hairpin i) in the translocation pause position, ii) dissociation, iii) folding back onto the trailing backbone and continuing to translocate the nanopore, iv) finally exiting the nanopore and beginning to refold. The nanopore response to the foldback position in step iii) can be a deep current state that can be used advantageously to discriminate sequentially identical reporter states (with sequentially identical current blockage levels). Choices of molecular building materials and other conjugation positions along the hairpin can be used to adjust this response.

(3) The "pendant hairpin" is a variant of the foldback hairpin that it simplifies synthesis. In this case the primary backbone is synthesized and the monomer consisting of a sequence complimentary to the duplex site is linked with a conjugation chemistry such as "Click" chemistry. The pendant monomer has sufficient steric mobility that it can hybridize with the duplex site. The structural difference in this design from the foldback hairpin is that the loop is replaced with a connector chemistry of suitable length.

(4) The "chimera hairpin" is a hairpin variant that can be assembled with unbranched synthesis. The backbone for this design passes through one strand of the duplex in the 3' to 5' direction continues through a connector chemistry such as PEG doubling back to the 5' end of the other duplex strand and continuing up through this strand and on to the next reporter section. This synthesis requires that the direction of synthesis flip between 3'→5' to 5'→3' and back again as the molecule is built.

(5) The "simple free duplex" is effective but may result in poor fill defined by the average fraction of duplex sites along the measured backbone that are unduplexed during measurement. To maintain high fill rate during translocation, the duplex requires a high kon/low koff and a sufficient background concentration of the complementary oligomer.

(6) The "circularized free duplex" also has a detached duplexing oligomer similar to the simple free duplex except that the duplexing oligomer is circularized. It can have 2 or more hybridization sites on the same molecule. Also the circularization impedes the detached oligomer from translocating the nanopore (hemolysin). This can restrict the molecule to 1 reservoir side and eliminates associated background translocation noise. Another feature is that its interaction with the pore forces the leading base pair in the duplex to open because the backbone continues to translocate whereas the circularized complement must follow the preceding bases back around. This can facilitate the duplex release at lower forces and prevents the lead base pair of the duplex from jamming into the pore.

(7) The "free hairpin duplex" is also similar to the simple free duplex except the duplexing oligomer has a hairpin extending from the leading base. This hairpin facilitates a lower force release of the duplex similar to the circularized free duplex. To prevent translocation it could also have an additional hairpin on its trailing end.

(8) The "anchored duplex" has a detached duplex oligomer that is tethered to an anchor. This anchor is a large cross-section molecule, molecular complex or nanoparticle. This requires a nanopore geometry that accepts the duplex to proceed but stops further translocation when the anchor cannot proceed. FIG. 9 shows an anchored duplex stopped during translocation of an alpha-hemolysin pore. In this case the anchor, indicated by the circular object, is stopped at the entrance to the vestibule which prevents further translocation due to the duplex stretched out in the vestibule. This design approach is also appropriate for other types of nanopores with large barrels that can accept double-stranded nucleic acid, but do not allow the anchor to pass. This leads to other types of coding which can use the length or composition of the duplexing oligomer (that is tethered to the anchor) in order to produce the measured signal due to its presence in the nanopore barrel.

The following examples are provided for purpose of illustration, and not for limitation.

EXAMPLES

Example 1

Foldback Hairpin

An experiment was performed that used the foldback hairpin duplex to perform TCH. A molecule was synthesized with 4 foldback hairpins to perform TCH for reporter segments ordered as: poly-A, poly-C6, poly-A and a poly-PEG6. In the case of the internal poly-A reporter, a connector of poly-PEG6 was added before the next hairpin. This ensured that in each case, when the first three hairpins opened up and began to translocate, they unfolded back along a "thin" backbone polymer (either poly-C6, poly-PEG6). This unfolded condition was still thin enough to translocate the nanopore constriction.

The experiment used 2M KCl with 10 mM HEPES at Ph 7.4 in two reservoirs separated by a PC lipid bilayer membrane that was supported on a 25 micron Teflon aperture (see Nahid Jetha et al. "Forming an α-Hemolysin Nanopore for Single-Molecule Analysis," Micro and Nano Technologies in Bioanalysis, vol. 544, R. S. Foote and J. W. Lee, Eds. Totowa, N.J.: Humana Press, 2009, pp. 113-127). A single WT alpha-hemolysin nanopore was embedded in the membrane. Open channel ion current was measured to be 247 pA under a voltage of 120 mV applied between Ag/AgCl electrodes positioned in each reservoir. The electrodes were connected with short leads to a CV 203BU head stage that connected to a Axopatch™ 200B amplifier (Molecular Devices, CA). Data was filtered with the amplifier's 10 kHz filter and digitized for data capture at 100 ksamples/s. The 4 inline hairpin molecule was introduced to the Cis reservoir to translocate the nanopore vestibule-first.

Figure 11:
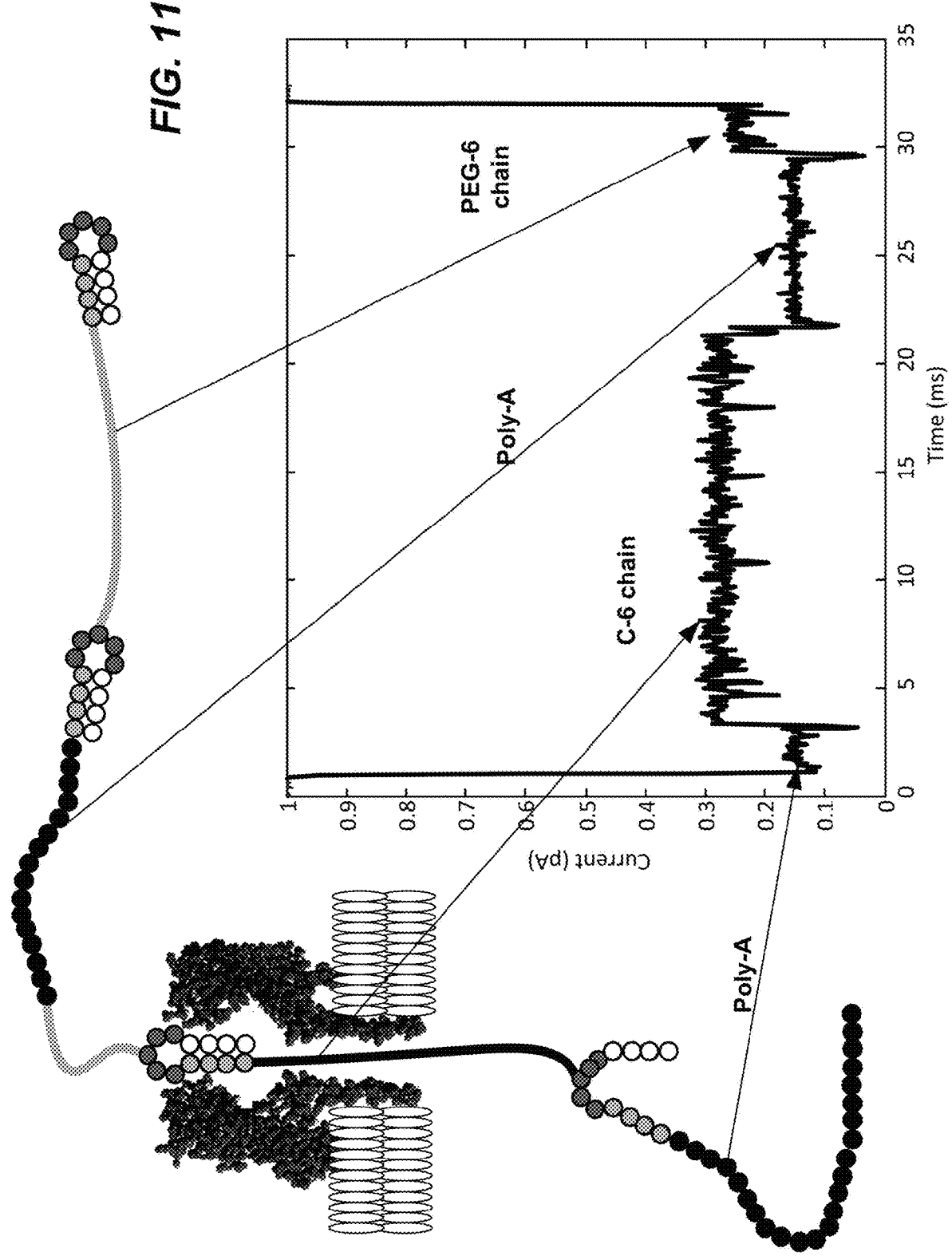
FIG. 11 depicts the current response of a translocation through a nanopore.

FIG. 11 show the current response of a translocation. The trace plots current in the vertical axis (normalized to open channel current) vs time expressed in milliseconds along the horizontal. The schematic of the molecule shows the response as each hairpin pauses at the constriction point in the vestibule. The variable ion current blockage level depends upon the reporter segment that is paused in the stem. The 4 reporters poly-A, poly-C-6, poly-A and a poly-PEG-6 correspond to 4 normalized current levels of 0.15, 0.28, 0.15 and 0.24. Note that at transitions between any 2 levels there is a deeper spike in the current that drops below 0.1. This corresponds to the blockage when the hairpin unfolds and must translocate its trailing edge overlapped with "thin" PEG6. This deep spike transition can be used to differentiate sequential states especially when the consecutive states are the same level. Note that in the terminal hairpin case there is no overlap and no deeper current spike occurs.

Example 2

Low Blocking Duplex

Figure 12:
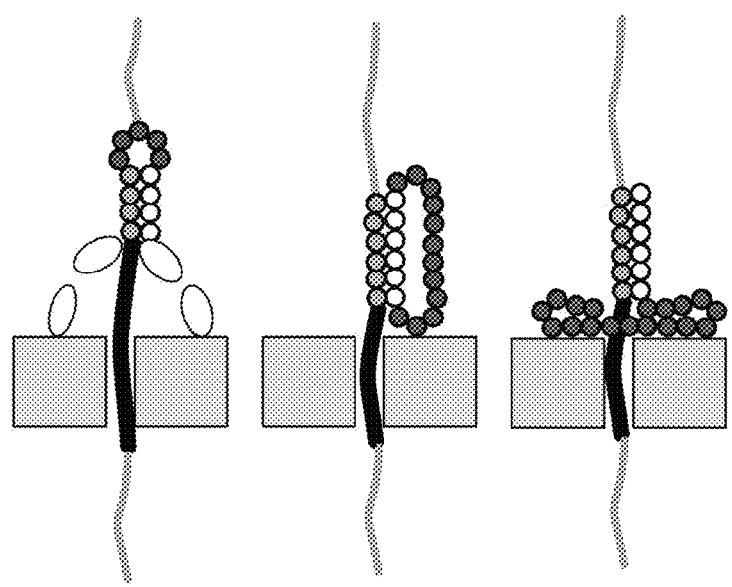
FIG. 12 depicts several alternate designs that increase ion current flow relative to the simple free duplex.

Dynamic range of the reporters is limited by the ion current blocking due to the duplex. Some duplex designs can reduce such blockage and increase dynamic range. FIG. 12 shows several alternate designs that increase ion current flow relative to the simple free duplex. In one embodiment, a porous structure or layer is placed in front of the nanopore which stops the duplex (and translocating molecule) but does not seriously impede the ion current flow. In another embodiment the duplex is a circularized free oligomer which reduces the distance that the end of the duplex can enter the nanopore and thus reduces ion current blockage. In the last embodiment the duplex is a single oligomer with 2 hairpins that fold back tightly to each other but have an additional overhang that forms the complementary portion that hybridizes to the translocating molecule.

Example 3

Voltage Control

The distribution of release times at a fixed voltage is generally exponential (attributed to a single simple release mechanism). This limits detection efficiency because data must be captured at a rate sufficient to measure the ion blockage level before the fastest release, but then must wait or capture excess data for all the other slower duplex releases. According to this distribution, if a sampling rate is chosen so 99.9% of the duplex releases are slow enough to measure at least one complete sample, then for average measurement time is 1000 samples long.

One embodiment used to improve this efficiency is to use redundant reporters. If a sampling rate is chosen so 99.9% of redundant reporter pairs have at least 1 of their 2 duplexes release slow enough to measure at least one complete sample, then for average measurement time per reporter is reduced to 32 samples long (64 samples for the redundant reporter pair). This technique can be extended to 3 or more redundant reporters to get additional improvements but at the expense of further extending the Xpandomer length.

In another method a force is selectively applied to the duplex at the nanopore for a short enough period that the duplex is stripped off but the next duplex that engages with nanopore is unaffected (i.e., does not have the force applied until the next selective application) or is no longer affected. The selective force can be delivered in different ways.

In one embodiment the selective force is applied using short, high-voltage pulses. During measurement the voltage is sufficiently low that the duplex remains stable but is high enough that the signal-to-noise is sufficient for measurement and identification of the reporter type. The slopes of the curves in FIG. 7 range from 0.19 dBt/mV for the A0 reporters to 0.37 dBt/mV for the A6 reporters (where dBt are the units for Rt=10 log(t1/t2) and t1 and t2 are release time values). Extrapolating linearly to voltages >300 mV, average duplex release times are in the microsecond regime.

Xpandomers can be designed so that a high voltage microsecond pulse sufficient to release a duplex will be complete before the Xpandomer translocates and stops at the next duplex. Increasing distance, reducing charge and providing frictional elements to slow the translocation between reporter duplexes can be adjusted to achieve this objective. By using this technique, after the pulse is finished, an incoming reporter construct duplex engages the nanopore under low voltage and the duplex is stable for measurement. After a measurement period another high voltage pulse is applied to release the duplex and translocate to the next duplex. Ideally the duplex release occurs at each pulse, but in cases where the pulse fails to release the duplex, the reporter undergoes one or more measurement/pulse cycles until release occurs.

Figure 13:
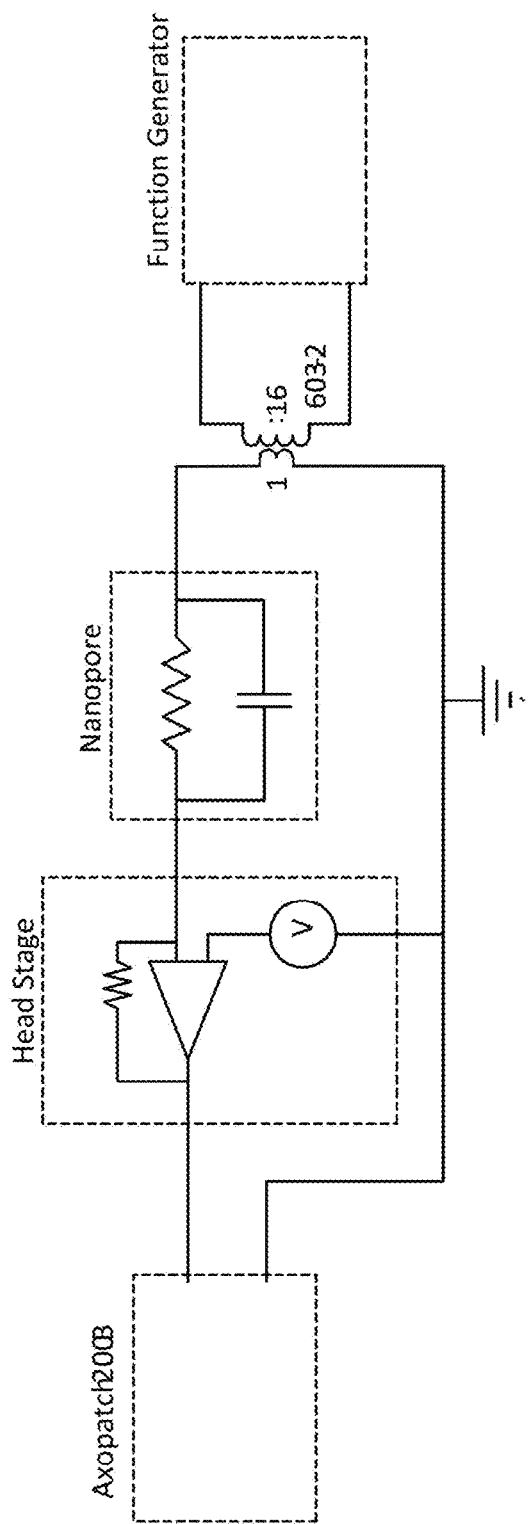
FIG. 13 is an electrical schematic that depicts delivery of short voltage pulses across a nanopore that minimizes the reactive response of the Axopatch™ 200B amplifier (Molecular Devices, CA) headstage. The nanopore is replaced with an equivalent circuit indicated by capacitor and resistor in parallel.

In this example, tethers had 6 duplexes along the backbone with ordered states A0, A4, A5, A6, A2 and A5. The experimental setup shown in FIG. 13 is as described by Jetha except that the ground return to the headstage was modified to pass through an inductor coil of a 603-2 current sense transformer (West Coast Magnetics, CA). The other coil in the transformer was connected to an 33120 A function generator (Hewlett Packard, CA) and driven with a fast rising 10 V pulse that immediately decayed in several microseconds, once every 2 ms. The output pulse that appeared across the transformer output was a similar shaped pulse of 1 V amplitude. Its decay was adjusted at the input to provide a FWHM of 3.4 ps. The Axopatch™ 200B amplifier (Molecular Devices, CA) was run with 100 mV DC applied to the headstage output, so the voltage applied across the nanopore was 100 mV DC plus a 1 V pulse applied once every 2 ms.

Figure 14:
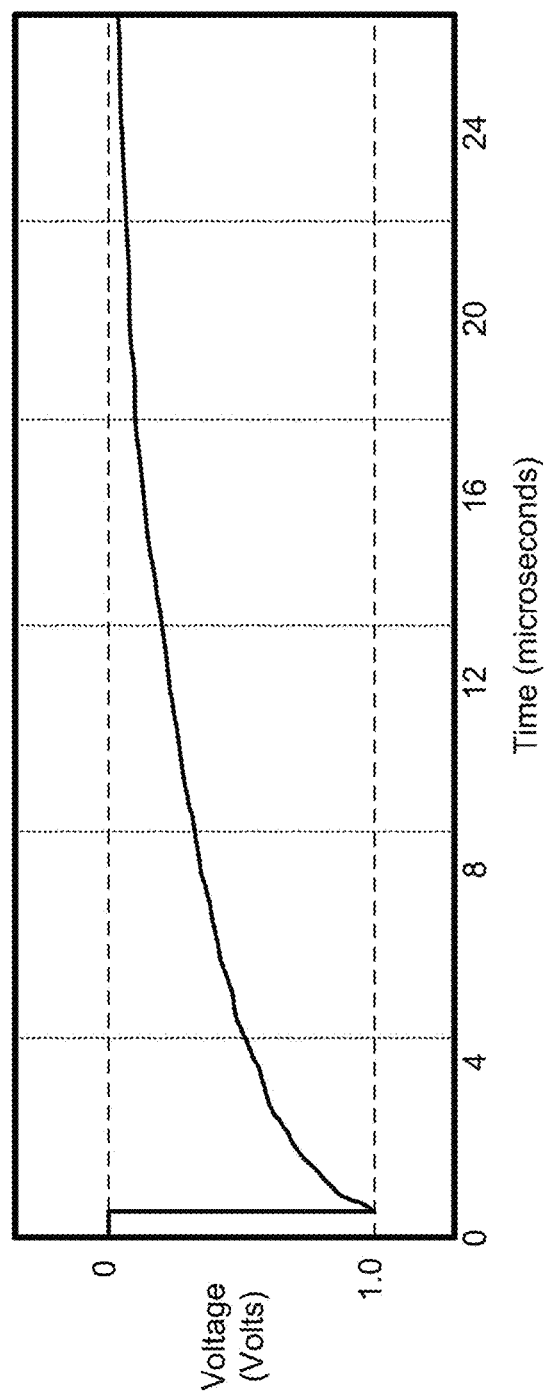
FIG. 14 depicts a representative voltage pulse applied periodically across the nanopore. Representative pulse periods range from 250 microseconds to 10 milliseconds, pulse widths range from 0.5 microseconds to 10 microseconds, and pulse amplitudes range from 300 mV to 2.0 V.

The oscilloscope trace, FIG. 14 shows the voltage pulse (1.0 volt) applied to the nanopore.

Figure 15:
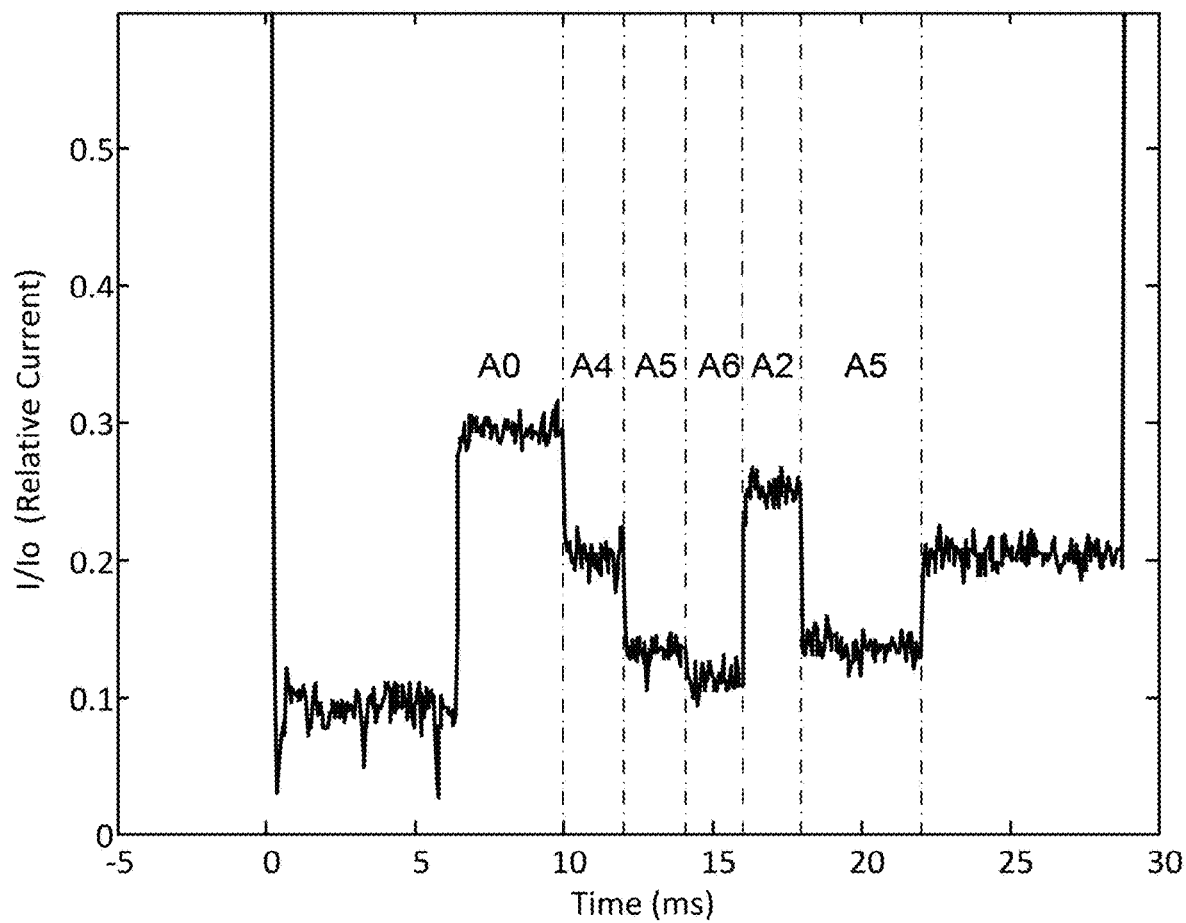
FIG. 15 depicts a data trace of relative ion current ($I/I_o$) through an alpha-hemolysin nanopore as a 6 reporter tether is translocated. The applied voltage across the nanopore was 100 mV DC (measured from trans to cis), superimposed with a 1.0 V pulse every 2 miliseconds (ms).

The trace shown in FIG. 15 indicates the 6 duplexed states along with unduplexed entry and exit levels. Each duplex release coincided with one of the pulses that occurred at 2 ms intervals. The middle 4 states were each 2 ms long on the first and last states required an additional pulse to release their duplexes.

Periodic release of the duplexes increases the efficiency of measurement because the shortest release can be timed to the minimum period required to acquire a reliable measurement. There is an additional efficiency in the design of the detector. Now measurements can be synchronized to the pulse frequency to as low as 1 per period, though more may be taken for quality purposes. A related efficiency is gained in analyzing the data afterwards because states will transition during a pulse, so state calling is simplified.

In another embodiment of controlled duplex release, the TCH complement has a small diameter gold nanocrystal (e.g., 1.4 nm) tethered covalently to its end so it lies distal to the nanopore when it is stopped during translocation of the reporter tether. After the reporter ion current blockage is measured, a short pulse of high frequency (e.g., 1 GHz) magnetic field is applied which couples to the gold particle and destabilizes the duplex that is already the voltage applied stress. The technique of opening duplexes was demonstrated by K. Hamad-Schifferli, et al. (Nature, vol. 415, no. 6868, pp. 152-155, January 2002), but has not been used in conjunction with nanopores.

Each of these methods with periodic clocks are well suited to array-based nanopores because they can be applied across all pores simultaneously. In the case of the voltage pulse technique the pulse can be applied across a common electrode.

Alternatively, if feedback were applied to each nanopore, forces could be applied continuously or pulse-wise until a release was detected and the force was removed to measure the next reporter.

Example 4

Flossing

The concept of flossing, reported in 2004 (Sánchez-Quesada, A. Saghatelian, S. Cheley, H. Bayley, and M. R. Ghadiri, "Single DNA Rotaxanes of a Transmembrane Pore Protein," Angewandte Chemie International Edition, vol. 43, no. 23, pp. 3063-3067, 2004), provides a method to efficiently read a single Xpandomer multiple times and establish a low error rate/read. This can be implemented multiple ways.

In one embodiment the Xpandomer sample is introduced on the cis side of the nanopore with no duplexes attached to the reporter construct sites and the free solution duplex complements are introduced on the trans side. The Xpandomer is terminally modified with a highly stable hairpin (or duplex) and has another high stability duplex site (initially unduplexed) on the leader. Under a negative potential, the Xpandomer leader is captured and the Xpandomer rapidly translocates the nanopore until it is stopped at the terminal hairpin. The voltage is quickly lowered before the hairpin dissociates, and prevents the Xpandomer from exiting. With the Xpandomer now in the trans-side, the duplex complements can now associate with the reporter construct sites along the Xpandomer. Also, the specific high stability leader duplex is now formed which prevents the Xpandomer from exiting from the leader side. The nanopore potential is now inverted and the Xpandomer is measured as it reverses out of the nanopore, stopping to release each reporter duplex, until the leader duplex is reached which will not release. Next, the potential is again inverted and the Xpandomer rethreads the nanopore for a second cycle of measurement. This can be repeated many times to establish a high fidelity consensus measurement.

To exit the nanopore after measurement, the Xpandomer is translocated to the terminal hairpin and a high voltage pulse is applied to release the hairpin. The Xpandomer exits to the trans-side and another Xpandomer is captured from the cis-side. One choice for the Xpandomer leader duplex is the fold-back hairpin type shown in FIG. 9 (alternative 3). In this type of hairpin, the leader will thread through the nanopore after the hairpin is released but when reforming, it prevents reverse translocation. In another embodiment, symmetric reporter constructs are designed to be read in either direction so that a reporter is positioned in the nanopore stem when the duplex stops in either direction. In this case the free solution duplexes are in both reservoirs and Xpandomer is measured in both translocation directions. In-line hairpins are well-suited for reporter construct duplexes when doing bidirectional measurement because of their inherent symmetry.

Creating arrays of biological nanopores is optimal when only one nanopore is inserted into the membrane that isolates each trans and cis well (often either the cis well is common to all nanopores). In addition, the ion current blockage often depends upon the direction an Xpandomer translocates through the nanopore. For example, the blockage currents can be different if a reporter enters from vestibule side or from the stem side of a hemolysin nanopore. This means that controlling the orientation of insertion of the nanopore in the membrane can affect performance. If flossing is used, the nanopore orientation is less important because the Xpandomer can be measured in either direction and more specifically in the preferred direction.

Example 5

Symmetric Tether

Figure 16A:
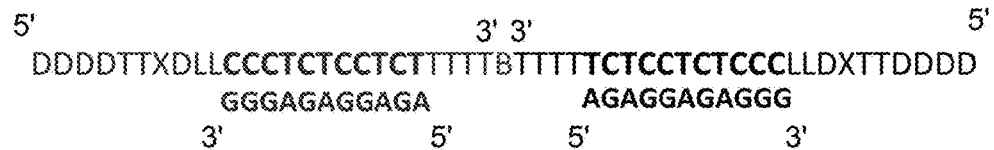
FIGS. 16A (SEQ ID NOS: 1 and 2) and 16B (SEQ NOS: 2 and 3) depict symbolic layouts of symmetric tethers having a mix of phosphoramidites, where 2 identical arms of each tether are synthesized from the brancher phosphoramidite depicted as "B".

An example of a Symmetric tether is shown in FIG. 16A The figure indicates a tether that is synthesized using phosphoramidite chemistry starting from a brancher shown as "B". Assembly proceeds along 2 branches with symmetric additions of the phosphoramidite monomers. The two branches are identical and are indicated in the figure with the 5' to 3' branch in blue (left of "B") and the 3' to 5' in black (right of "B"). Complements to the branch duplex sites are also shown. The tether symmetry means it looks and measures the same when it is flipped end-to-end. This attribute means that if flossing is used for measurement an Xpandomer with symmetric tethers can be measured when translocated in either direction. Generally, the final synthesis step of an X-NTP is to conjugate each end of a tether specifically to each of two conjugation points on a modified NTP construct. Synthesis with the symmetric tether eliminates the need for the conjugations to be specific which simplifies the process.

Figure 16B:
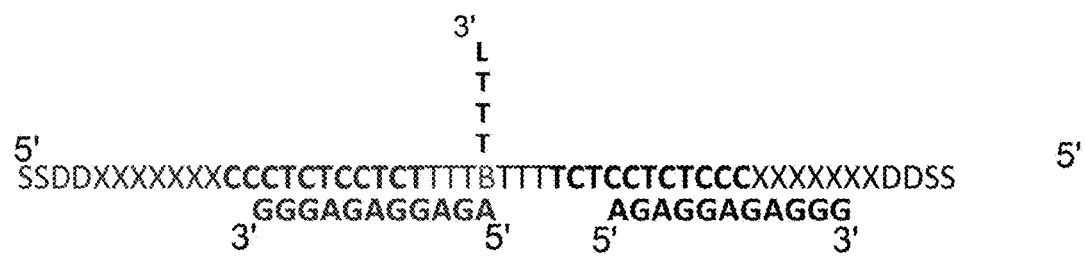
Figure 17:
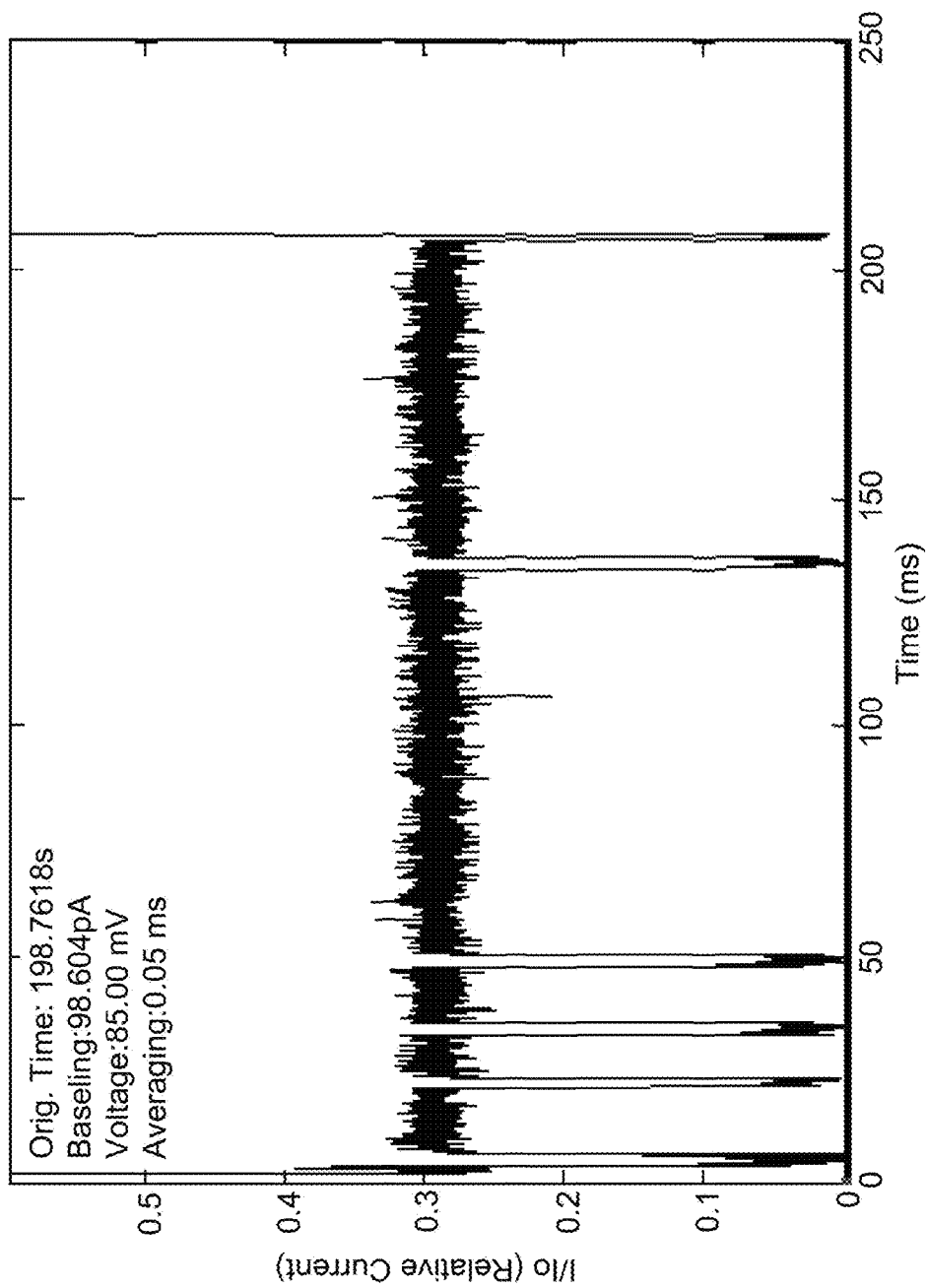
FIG. 17 depicts a representative current trace of an Xpandomer synthesized from sequential incorporation of 6 X-NTP with tethers that are schematically represented in FIG. 16B.

FIG. 16B shows another symmetric tether. Compared to the tether in FIG. 16A, this tether has a different reporter code and also has a third arm, LTTT that is synthesized before the brancher phosphoramidite is attached. This third arm contributes to a deep blockage state when it folds onto the backbone during translocation of a hemolysin nanopore and is stalled in the nanopore barrel by the second duplex along the tether. The deep state can be used advantageously as a clock signal to discriminate between homopolymer bases. This tether construct was incorporated into a cytosine X-NTP. DPo4 polymerase was used to extend a primer to complement a 10-base guanidine homopolymer template. This Xpandomer extension product was cleaved in an acid solution and its duplex sites were hybridized to the 10-base complements shown in FIGS. 16A and 16B. The Xpandomer was then measured in a hemolysin nanopore under 85 mV applied potential. Both reservoirs had 10 mM HEPES and pH 7.4, with 2.0 molar NH$_4$Cl on the trans reservoir and 1.0 molar NH$_4$Cl on the cis reservoir. FIG. 17 shows the translocation of one of these Xpandomers with 6 X-NTP incorporations. As each tether translocates the nanopore the reporter state of I/I$_o$=0.30 is measured followed by a deep state of I/I$_o$=0.04. The high state is due to the low ion blocking cross-section of the string of 7 PEG-3 phosphoramidites (XXXXXXX in FIG. 16B) preceding the first duplex into the nanopore. The low state is due to high ion blocking when the third arm folds back on the backbone (LTTT folds at the brancher B onto the TTTT in FIG. 16B) as it precedes the second duplex into the nanopore. Here the deep state is a clock that distinguishes 6 consecutive identical reporter states.

Example 6

X-NTP Tether

X-NTPs are designed with a tether comprising a single reporter selected from 4 possible states, a pendant hairpin for TCH and followed by a section of PEG. Xpandomers are formed by template dependent polymerase extension of these X-NTPs. A hemolysin nanopore measurement system is prepared with 50 microliters of 2 M KCl in a 7.0 pH aqueous buffer in both cis and trans reservoirs. 500 fmoles of Xpandomer sample with the same buffer is added to the cis well. A voltage is applied between cis and trans reservoirs that is 60 mV DC with 1V pulses at 2 ms periods. Each pulse rises rapidly to the 1 volt maximum and decays to the DC level with a 2 microsecond exponential fall time. Xpandomer translocates the nanopore rapidly but stops at each pendant hairpin along its length. At each stoppage, the ion current blockage level of the associated reporter is measured under the 60 DC applied voltage, identifying the base of the incorporated X-NTP. When the periodic pulse is applied, the translocation force increases and opens pendant hairpin, folding back the pendant group onto a trailing PEG section which are pulled through the nanopore together until another pendant hairpin stops the translocation. The pulse is short enough that when the next pendant hairpin engages with the nanopore, the voltage is back to 60 mV DC.

Example 7

Alternative TCH Reporters

Figure 18:
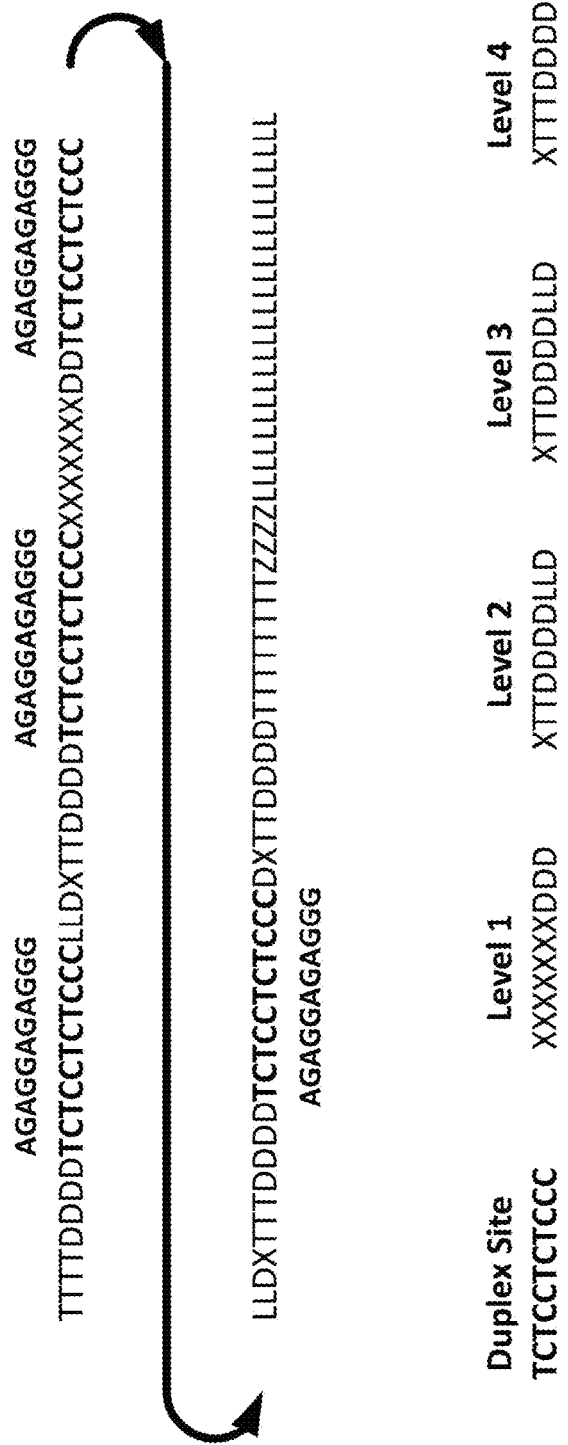
FIG. 18 depicts a tether constructed of 4 reporter constructs and a leader. Each reporter construct has an 11 base duplex site (SEQ ID NO: 4) that is indicated along with its complementary duplex (SEQ ID NO: 2). The 4 reporters are each composed of a specific arrangement of phosphoramidites chosen from triethylene glycol (X), hexaethylene glycol (D), ethane (L) and deoxythymine (T).

A variety of other TCH reporter structures have been synthesized using the phosphoramidite monomer set described in Table 1 above. The example described here used a construct synthesized on a MerMade 12 (Bioautomation, TX) with 126 phosphoramidite monomers. The sequence is shown in FIG. 18 and contains a leader portion T8 Z4 L25 followed by 4 reporter constructs. The leader facilitates threading of the construct through the nanopore. The duplex site on each reporter construct is an 11 base sequence that will hybridize to its 11 base complement to provide TCH for the reporters. The experiment used buffers of 1M NH4Cl with 10 mM HEPES at Ph 7.4 in the cis reservoir and 2M NH4Cl with 10 mM HEPES at Ph 7.4 in the trans reservoir. The reservoirs were separated by a lipid bilayer membrane that was supported on a 25 micron Teflon aperture using a fixture described by Jetha.

Figure 19:
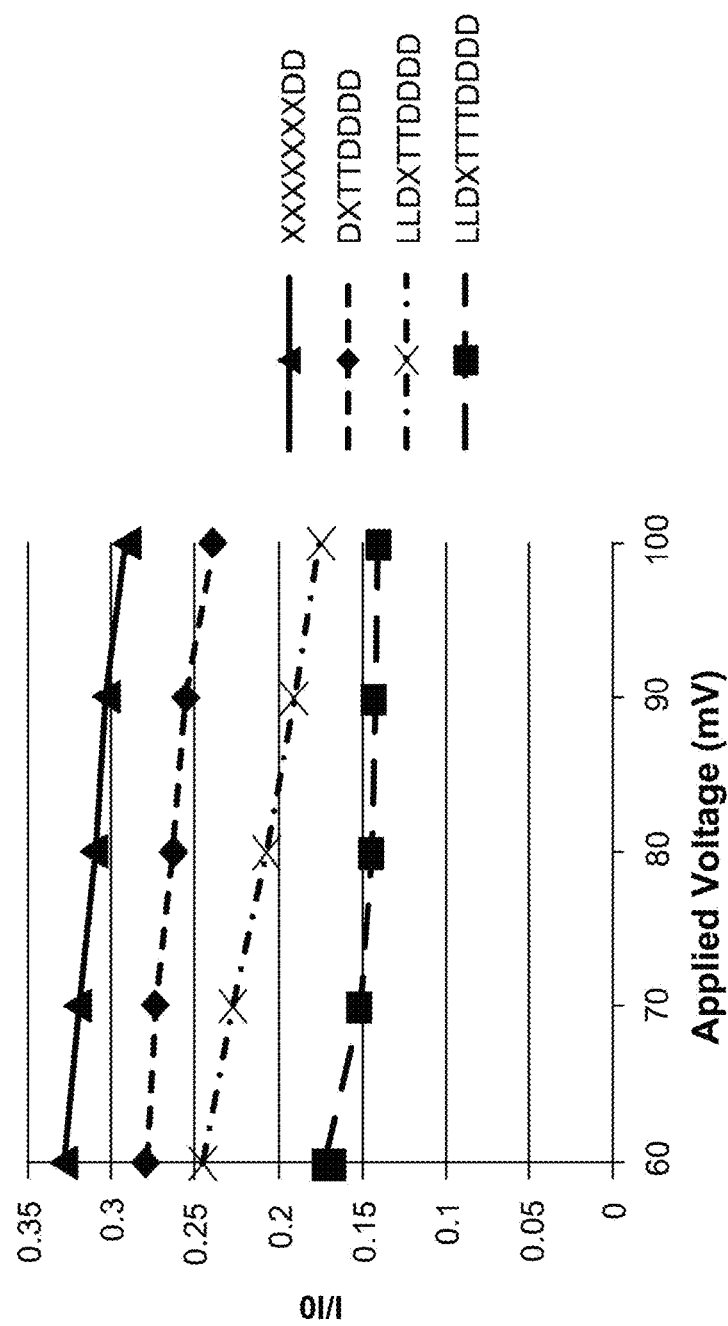
FIG. 19 depicts the relative ion current data as a function of applied voltage across the nanopore for each of the 4 reporter constructs described in FIG. 18.
Figure 20:
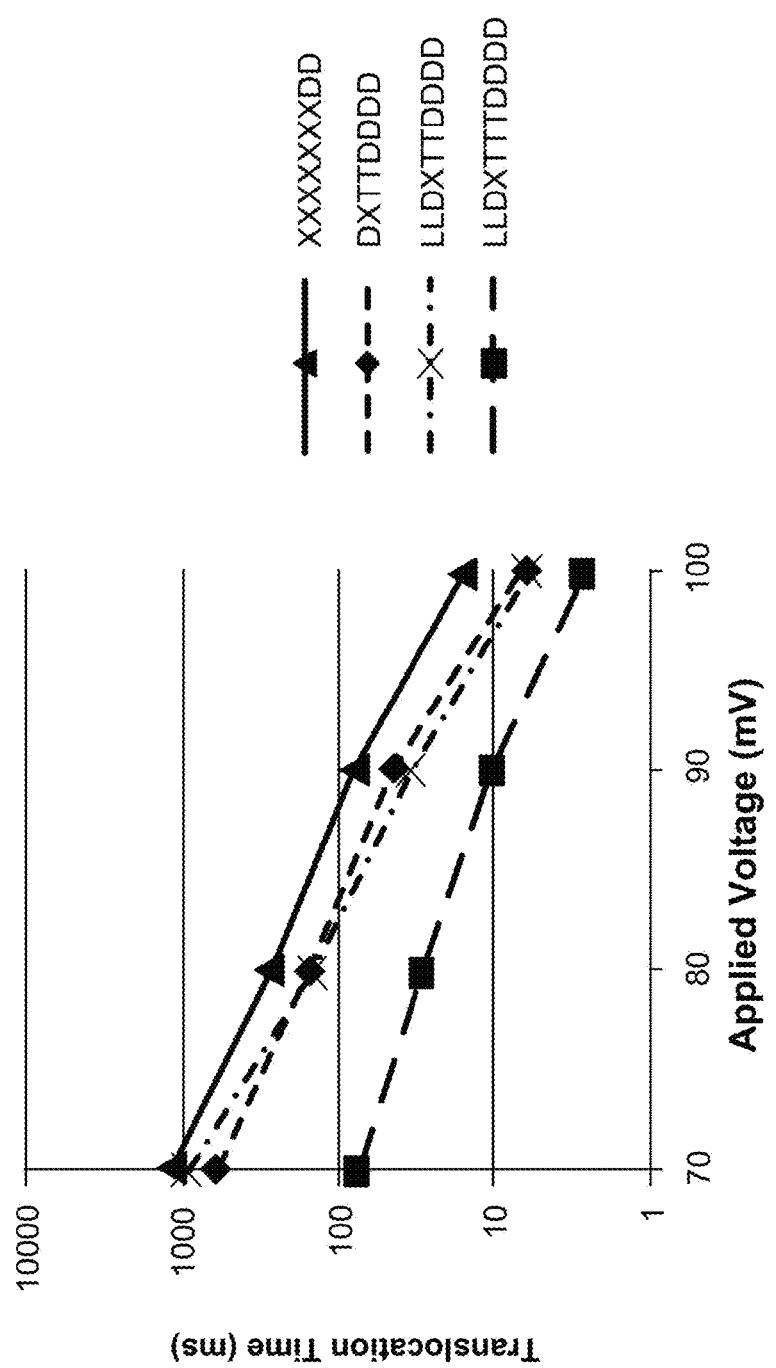
FIG. 20 depicts the release times of the duplexes as a function of applied DC voltage (with no pulsing) across the nanopore for each of the 4 reporter constructs described in FIG. 18.

A single WT alpha-hemolysin nanopore was embedded in the membrane. Open channel ion current was measured to be 247 pA under a voltage of 120 mV applied between Ag/AgCl electrodes positioned in each reservoir. The electrodes were connected with short leads to a CV 203BU head stage that connected to a Axopatch™ 200B amplifier (Molecular Devices, CA). Data was filtered with the amplifier's 10 kHz filter and digitized for data capture at 100 ksamples/ s. Full translocation events were indicated in the data by current blockages with the 4 state levels as expected. These events were analyzed to determine the average relative ion current blockage (I/Io) and average lifetime for each of the four states. This data is presented as a function of applied voltage across the nanopore in FIG. 19 and FIG. 20.

Figure 21:
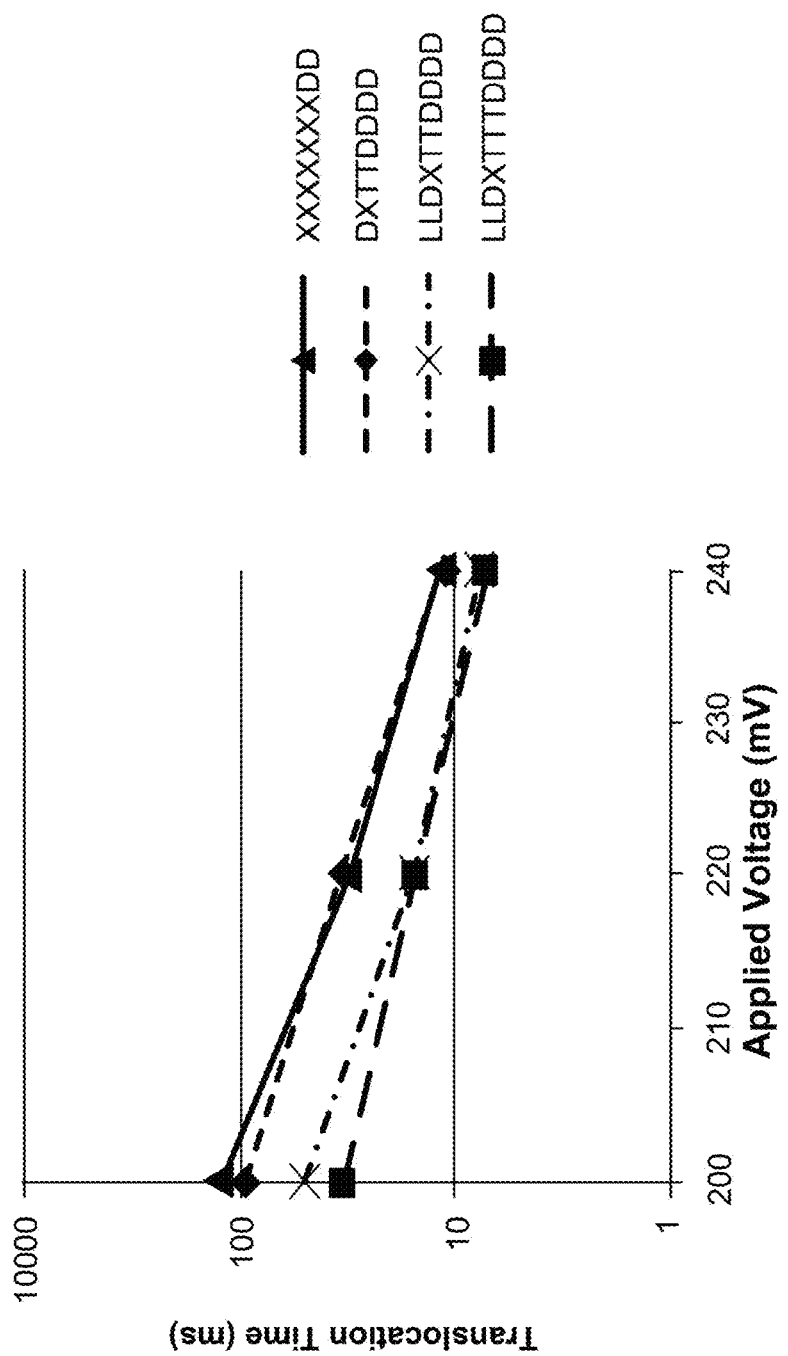
FIG. 21 depicts the release times of the duplexes as a function of peak pulse voltage applied at 2 ms intervals (superimposed on a constant 60 mV DC baseline) applied across the nanopore for each of the 4 reporter constructs described in FIG. 18.

As shown in FIG. 21, additional data was captured in the same experimental conditions using an applied voltage of 60 mV and an applied voltage pulse. Pulses were applied every 2 ms by programming the Axopatch™ 200B (Molecular Devices, CA) directly with a programmed pulse (without the use of the transformer shown in FIG. 14). The programmed pulse was triangular in shape with a rise and fall ramp rate of 20 mV/microsecond and the pulse length is determined by the peak pulse voltage. The time constant for the duplex release of these reporters is ~10 ms with the 240 mV peak pulse and 60 my DC. An average release time of 10 ms means that on average it required five of the pulses to release the duplex.

FIGS. 4 and 18 depict sets of reporters that are designed to produce ion current signals in alpha hemolysin nanopores that are easily differentiated from each other and that maximize the use of the dynamic range. Dynamic range is maximized by selecting a backbone of low impedance molecules (polymers), typically those with small physical cross-sections and low linear mass densities. When a reporter is composed of only these molecules, the $I/I_o$ is the highest. $I/I_o$ levels for poly-PEG6 (FIG. 6A-B), poly-C-6 (FIG. 11) and poly-PEG-3 (FIG. 19) were 0.27, 0.28, and 0.29-0.33, respectively. In each case these values also depend upon other experimental conditions, electrolytes, TCH duplex, and the like, but these reporters establish the highest $I/I_o$ in the dynamic range. This low impedance group of molecules includes polyethylene glycol, poly-abasic, and poly aliphatic polymers. To produce lower $I/I_o$ levels that range down to <0.1, molecules are chosen from the group of high impedance molecules (those with large physical cross-sections and high linear mass density), including A, C, G and T. Positioning additional high impedance molecules in the backbone of low impedance molecules increasingly lowers these levels.

It should also be noted that while these THC reporter constructs and methods have been described in the context of Xpandomers, they have more generalized use in labelling of analytes in many other applications, including (for example, biological or nanoparticle labelling assays.

Exemplary embodiments include the following:

Embodiment 1

A method for controlling the translocation of a target molecule for sensing by a nanopore, comprising passing the target molecule through the nanopore subjected to a base line voltage and a pulsed voltage, wherein the target molecule comprises two or more duplex features which provide translocation control by hybridization.

Embodiment 2

The method of embodiment 1, wherein the two or more duplex features which provide translocation control by hybridization are selected from the group consisting of an in-line hairpin, a foldback hairpin, a pendant hairpin, a chimera hairpin, a simplex free duplex, a circularized free duplex, a free hairpin duplex, and an anchored duplex.

Embodiment 3

The method of any one of embodiments 1 or 2, wherein the pulsed voltage is sufficient to release the duplex feature engaged with the nanopore, while leaving the next duplex feature of the target molecule to engage with the nanopore unaffected.

Embodiment 4

The method of any one of embodiments 1-3, wherein the pulsed voltage has a duration of less than 100 microseconds, less than 50 microseconds, less than 10 microseconds, less than 5 microseconds, or less than 1 microseconds.

Embodiment 5

The method of any one of embodiments 1-4, wherein the pulsed voltage has a voltage of greater than 0.2 volts, greater than 0.5 volts, greater than 1 volt, or greater than 10 volts.

Embodiment 6

The method of any one of embodiments 1-4, wherein the pulsed voltage is 1 volt.

Embodiment 7

The method of any one of embodiments 1-6, wherein the periodicity of the pulsed voltage ranges from 50 Hz to 10 kiloHz.

Embodiment 8

The method of any one embodiments 1-6, wherein the periodicity of the pulsed voltage is 500 Hz.

Embodiment 9

The method of any one of embodiments 1-8, wherein the target molecule is sensed by the nanopore during the time period between pulses of the pulsed voltage.

Embodiment 10

The method of embodiment 3, wherein the duplex feature of the target molecule is released upon each pulse of the pulsed voltage.

Embodiment 11

The method of embodiment 3, wherein the duplex feature of the target molecule is released upon multiple pulses of the pulsed voltage.

Embodiment 12

A reporter construct comprising a low impedance polymer and a high impedance polymer.

Embodiment 13

The reporter construct of embodiment 12, wherein the low impedance polymer comprises triethylene glycol (X),

Embodiment 14

The reporter construct of embodiment 12 or 13, wherein the high impedance polymer comprises deoxyadenosine (A), deoxythymine (T), deoxycytosine (C), or deoxyguanodine (G), or combinations thereof.

Embodiment 15

A reporter construct comprising two or more phosphoramidites selected from the group consisting of triethylene glycol (X), hexaethylene glycol (D), ethane (L), hexane (P), dodecane (Z), deoxyadenosine (A), deoxythymine (T), deoxycytosine (C), deoxyguanodine (G) and abasic (Q), and wherein the reporter construct comprises at least one of X, D, L, P, Z or Q.

Embodiment 16

The reporter construct of embodiment 15, comprising an A0 reporter as set forth in FIG. 4.

Embodiment 17

The reporter construct of embodiment 15, comprising an A2 reporter as set forth in FIG. 4.

Embodiment 18

The reporter construct of embodiment 15, comprising an A4 reporter as set forth in FIG. 4.

Embodiment 19

The reporter construct of embodiment 15, comprising an A6 reporter as set forth in FIG. 4.

Embodiment 20

The method of embodiment 1, wherein the target molecule comprises a reporter construct of any one of embodiments 12-19.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, including U.S. Provisional Application No. 61/996,824, filed on May 14, 2014, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for controlling the translocation of a target molecule for sensing by a nanopore, comprising passing the target molecule through the nanopore subjected to a base line voltage and a pulsed voltage, wherein the target molecule comprises two or more features which provide translocation control by steric hindrance, and wherein the periodicity of the pulsed voltage ranges from between greater than 100 Hz (10 milliseconds) to 4,000 Hz (250 microseconds).

2. The method of claim 1, wherein the pulsed voltage is sufficient to allow translocation of the feature engaged with the nanopore by steric hindrance, while leaving the next feature of the target molecule free to engage with the nanopore.

3. The method of claim 2, wherein the feature of the target molecule engaged with the nanopore by steric hindrance translocates upon each pulse of the pulsed voltage.

4. The method of claim 2, wherein the feature of the target molecule engaged with the nanopore by steric hindrance translocates upon multiple pulses of the pulsed voltage.

5. The method of claim 1, wherein the target molecule is sensed by the nanopore during the time period between pulses of the pulsed voltage.

6. The method of claim 1, wherein the periodicity of the pulsed voltage is 500 Hz (2 milliseconds).

7. The method of claim 1, wherein the pulsed voltage has a duration of less than 100 microseconds.

8. The method of claim 1, wherein the pulsed voltage has a duration of less than 50 microseconds.

9. The method of claim 1, wherein the pulsed voltage has a duration of less than 10 microseconds.

10. The method of claim 1, wherein the pulsed voltage has a duration of less than 5 microseconds.

11. The method of claim 1, wherein the pulsed voltage has a duration of less than 1 microsecond.

12. The method of claim 1, wherein the pulsed voltage has a voltage of greater than 0.2 volts.

13. The method of claim 1, wherein the pulsed voltage has a voltage of greater than 0.5 volts.

14. The method of claim 1, wherein the pulsed voltage is 1 volt.

15. The method of claim 1, wherein the pulsed voltage has a voltage of greater than 1 volt.

16. The method of claim 1, wherein the pulsed voltage has a voltage of greater than 10 volts.

17. The method of claim 1, wherein the target molecule comprises a reporter construct.

18. The method of claim 17, wherein the reporter construct comprises a low impedance polymer that produces an $I/I_o$ value of 0.27 or greater upon translocation through the nanopore, and a high impedance polymer that produces an $I/I_o$ value of less than 0.27 upon translocation through the nanopore.

19. The method of claim 17, wherein the reporter construct comprises triethylene glycol (X), hexaethylene glycol (D), ethane (L), hexane (P), dodecane (Z), or abasic (Q), or combinations thereof.

20. The method of claim 17, wherein the reporter construct comprises deoxyadenosine (A), deoxythymine (T), deoxycytosine (C), or deoxyguanodine (G), or combinations thereof.

21. The method of claim 17, wherein the reporter construct comprises two or more phosphoramidites selected from the group consisting of triethylene glycol (X), hexaethylene glycol (D), ethane (L), hexane (P), dodecane (Z), deoxyadenosine (A), deoxythymine (T), deoxycytosine (C), deoxyguanodine (G) and abasic (Q), and wherein the reporter construct comprises at least one of X, D, L, P, Z or Q.

* * * * *

```
                        SEQUENCE LISTING

<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Synthetic phosphoramidite construction

<400> SEQUENCE: 1
ccctctcctc ttttt                                                   15

<210> SEQ ID NO 2
<211> LENGTH: 11
<212> TYPE: DNA
<213> ORGANISM: Artificial Sequence
<220> FEATURE:
<223> OTHER INFORMATION: Complementary duplex of synthetic
      phosphoramidite construction

<400> SEQUENCE: 2
agaggagagg g                                                       11

<210> SEQ ID NO 3
<211> LENGTH: 14
<212> TYPE: DNA
<213> ORGANISM: Artificial Sequence
<220> FEATURE:
<223> OTHER INFORMATION: Synthetic phosphoramidite construction

<400> SEQUENCE: 3
ccctctcctc tttt                                                    14
```

```
<210> SEQ ID NO 4
<211> LENGTH: 11
<212> TYPE: DNA
<213> ORGANISM: Artificial Sequence
<220> FEATURE:
<223> OTHER INFORMATION: Synthetic phosphoramidite construction (duplex
      site)

<400> SEQUENCE: 4
ccctctcctc t                                                              11
```